United States Patent
Caille et al.

Patent Number: 5,599,830
Date of Patent: Feb. 4, 1997

[54] SULPHOROUS DERIVATIVES OF IMIDAZOLE AND THEIR USE AS MEDICAMENTS

[75] Inventors: Jean C. Caille, Paris; Alain Corbier, Le Buisson; Michel Fortin, Paris; Gilles Hamon, Le Raincy; Simone Jouquey, Paris; Jean P. Vevert, Pantin, all of France

[73] Assignee: Roussel Uclaf, France

[21] Appl. No.: 369,909

[22] Filed: Jan. 9, 1995

Related U.S. Application Data

[62] Division of Ser. No. 838,289, filed as PCT/FR91/00543 Jul. 4, 1991, Pat. No. 5,412,101.

[30] Foreign Application Priority Data

Jul. 5, 1990 [FR] France ................... 90 08538
Apr. 19, 1991 [FR] France ................... 91 04882

[51] Int. Cl.$^6$ ............ C07D 403/10; C07D 233/42; A61K 31/41; A61K 31/415
[52] U.S. Cl. ............ 514/398; 514/399; 514/381; 548/253; 548/307.1; 548/308.1
[58] Field of Search ............ 548/253, 308.1, 548/307.1; 514/381, 398, 399

Primary Examiner—David B. Springer
Attorney, Agent, or Firm—Bierman & Muserlian

[57] ABSTRACT

The invention relates to the products:

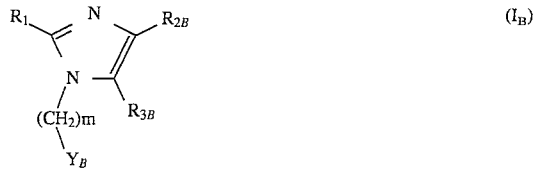

(I$_B$)

in which:
$R_1$=alkyl, alkenyl, alkynyl, alkylthio,
$R_{2B}$, $R_{3B}$ representing:
  hydrogen, mercapto, formyl, acyl, carboxy nitro, cyano,
  —PO$_3$(R)$_2$, R representing hydrogen, alkyl, aryl, amino or carbamoyl,
  the $R_{4B}$ radicals;

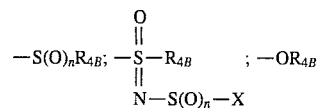

n=0 to 2
X'=aryl
$R_{4B}$ either represents —(CH$_2$)$_{m1}$—S(O)$_{m2}$—X—R$_{10}$, m1=0 to 4, m2=0 to 2
either m1 is different from 0, X—R$_{10}$ represents amino, or whatever m1 is, X represents a single bond or —NH—, —NH—CO—, —NH—CO—NH—,
$R_{10}$=alkyl, alkenyl or aryl, or hydrogen, alkyl, alkenyl, alkynyl, acyl or amino,
—S—S—R$_{4B}$', R$_{4B}$' represents R$_{4B}$ except for amino and alkoxy, and one of R$_{2B}$ and R$_{3B}$ represents —OR$_{4B}$:

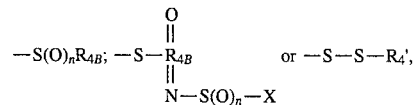

m=0 to 2,
Y$_B$—Y$_{1B}$—B—Y$_{2B}$,
Y$_{1B}$=aryl,
B=a single bond or —CO—, —O—, —NH—CO—, —CO—NH—, —O—O—(CH$_2$)$_p$—,
p=1 to 3,
Y$_{2B}$ represents hydrogen, cyano, carboxy, in all isomer forms and salts, their use as medicaments.

4 Claims, No Drawings

SULPHOROUS DERIVATIVES OF IMIDAZOLE AND THEIR USE AS MEDICAMENTS

PRIOR APPLICATION

This application is a division of U.S. patent application Ser. No. 838,289 filed Jul. 24, 1992, now U.S. Pat. No. 5,412,101 which is a 371 of PCT/FK91/00543 filed Jul. 4, 1991.

The present invention relates to new sulphurous derivatives of imidazole, their preparation process, the new intermediates obtained, their use as medicaments and the pharmaceutical compositions containing them.

A subject of the present invention is the products of formula $(I_B)$:

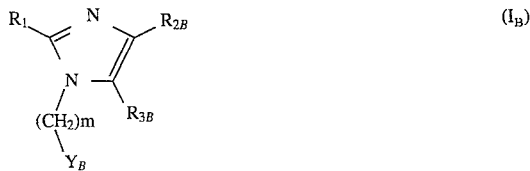

in which:

$R_1$ represents an alkyl, alkenyl, alkynyl, or alkylkhio radical, each of these radicals being linear or branched and containing at most 10 carbon atoms, or a cycloalkyl radical containing 3 ko 7 carbon atoms, all khese radicals being optionally substituted by one or more identical or different radicals chosen from halogen atoms, and the following radicals, hydroxyl, alkoxy containing at most 6 carbon atoms, alkylthio, acyl, free, salified or esterified carboxy, cyano, nitro, amino optionally substituted by one or two identical or different alkyl radicals containing at most 6 carbon atoms, cycloalkyl containing 3 to 7 carbon atoms and aryl opkionally substituted by one or more identical or different radicals chosen from halogen atoms, and khe following radicals, hydroxyl, alkyl, alkenyl and alkoxy containing at most 6 carbon atoms, haloalkyl, alkylthio, haloalkylkhio, haloalkoxy, aryloxy, arylalkoxy, carbamoyl, acyl, acyloxy, free, salified or esterified carboxy, tetrazolyl, cyano, nitro, amino optionally substituted by one or two identical or different alkyl radicals containing at most 6 carbon atoms and phenyl optionally substituted by one or more radicals chosen from halogen atoms, and the following radicals, hydroxyl, alkyl and alkoxy containing at most 4 carbon atoms, trifluoromethyl, free, salified or esterified carboxy and tetrazolyl, $R_{2B}$ and $R_{3B}$, identical or different, are chosen from:

a) the hydrogen atom, the following radicals: mercapto, formyl, acyl, free, salified or esterified carboxy, nitro, cyano, $-PO_3(R)_2$ in which R represents a hydrogen atom, an alkyl or aryl radical, amino or carbamoyl radicals optionally substituted by one or two radicals chosen from the $-(CH_2)_{m1}-S(O)_{m2}-X-R_{10}$ group as defined below and alkyl and alkinyl radicals, having at most 4 carbon atoms, b) the radicals $R_{4B}$,

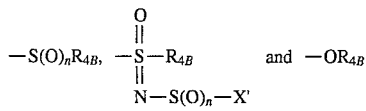

in which:

n represents the values 0, 1 or 2,

X' represents an aryl radical optionally substituted by one or more identical or different radicals chosen from halogen atoms, the following radicals: hydroxyl, alkyl, alkenyl and alkoxy containing at most 6 carbon atoms, haloalkyl, alkylthio, haloalkylthio, haloalkoxy, aryloxy, arylalkoxy, carbamoyl, acyl, acyloxy, free, salified or esterified carboxy, tetrazolyl, cyano, nitro, amino optionally substituted by one or two identical or different alkyl radicals containing at most 6 carbon atoms and phenyl optionally substituted by one or more radicals chosen from halogen atoms, and the following radicals: hydroxyl, alkyl and alkoxy containing at most 4 carbon atoms, trifluoromethyl, free, salified or esterified carboxy and tetrazolyl, and either $R_{4B}$ represents a $-(CH_2)_{m1}-S(O)_{m2}-X-R_{10}$ radical in which ml represents an integer from 0 to 4, m2 represents an integer from 0 to 2, preferably 2, and either when ml is not 0, $X-R_{10}$ represents an amino radical optionally substituted by one or two alkyl radicals containing at most 6 carbon atoms, or whatever the value of m1, X represents a single bond or the radicals $-NH-$, $-NH-CO-$ and $-NH-CO-NH-$, and $R_{10}$ represents an alkyl, atkenyl or aryl radical, these radicals being optionally substituted by one or more different or identical radicals chosen from halogen atoms, and the following radicals: hydroxyl, alkoxy containing at most 6 carbon atoms, alkylthio, acyl, free, salified or esterified carboxy, cyano, nitro, amino optionally substituted by one or two identical or different alkyl radicals containing at most 6 carbon atoms, cycloalkyl containing 3 to 7 carbon atoms and aryl optionally substituted by one or more different or identical radicals chosen from halogen atoms, the radicals hydroxyl, alkyl, alkenyl and alkoxy containing at most 6 carbon atoms, haloalkyl, alkylthio, haloalkylthio, haloalkoxy, aryloxy, arylalkoxy, carbamoyl, acyl, acyloxy, free, salified or esterified carboxy, tetrazolyl, cyano, nitro, amino optionally substituted by one or two different or identical alkyl radicals containing at most 6 carbon atoms and phenyl optionally substituted by one or more radicals chosen from halogen atoms, hydroxyl radicals, alkyl and alkoxy radicals containing at most 4 carbon atoms, trifluoromethyl radicals, free, salified or esterified carboxy radicals and tetrazolyl radicals, or $R_{4B}$ represents the hydrogen atom, or a radical chosen from alkyl, alkenyl, alkynyl and acyl, each of these radicals being linear or branched and containing at most 6 carbon atoms, and being optionally interrupted by one or more heteroatoms chosen from sulphur, oxygen or nitrogen atoms, or $R_{4B}$ represents an amino radical optionally substituted by one or two identical or different alkyl radicals containing at most 6 carbon atoms, a cycloalkyl radical containing 3 to 6 carbon atoms or an aryl radical, the alkyl alkenyl, cycloalkyl and aryl radicals being optionally substituted by one or more identical or different radicals chosen from:

halogen atoms, hydroxyl, haloalkyl, alkylthio, alkenylthio, alkynylthio, mercapto, acylthio, haloalkylthio, haloalkoxy, cyano, azido, nitro radicals, the $-O-Si(R_5)_3$ or $-Si(R_5)_3$ radical in which $R_5$ represents an alkyl radical containing at most 4 carbon atoms, aryl, arylalkyl, arylalkenyl, arylthio, aryloxy and arylalkoxy radicals in which, if appropriate, the alkyl, alkenyl and alkoxy radicals contain at most 6 carbon atoms and the aryl radical is optionally substituted by one or more identical or different radicals chosen from halogen atoms, hydroxyl, alkyl, alkenyl and alkoxy radicals containing at most 6 carbon atoms, haloalkyl, alkylthio, haloalkylthio, haloalkoxy, aryloxy, arylalkoxy, carbamoyl, acyl, acyloxy, free, salified or esterified carboxy, tetrazolyl, cyano, nitro, amino optionally substituted by one or two identical or different alkyl radicals containing at most 6 carbon atoms and phenyl optionally substituted by one or more radicals chosen from halogen atoms, hydroxyl radicals, alkyl and alkoxy radicals containing at most 4 carbon atoms, trifluoromethyl radicals, free, salified or esterified carboxy radicals and tetrazolyl radicals, alkyl, alkenyl and alkoxy radicals containing at most 6 carbon atoms, free, salified or esterified carboxy radicals, tetrazolyl, acyl, formyl, acyloxy, and —SO₃H radicals, and the radicals

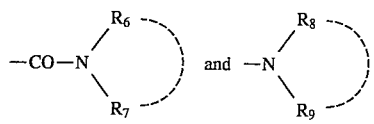 and 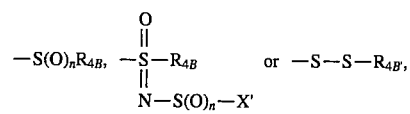

in which:
either $R_6$ and $R_7$ or $R_8$ and $R_9$, identical or different, are chosen from:

the hydrogen atom, amino acids, alkyl and alkenyl radicals containing at most 6 carbon atoms and optionally substituted by one or more identical or different radicals chosen from halogen atoms, the hydroxyl radical or alkoxy radicals containing at most 6 carbon atoms, the aryl, arylalkyl and arylalkenyl radicals in which the linear or branched alkyl and alkenyl radicals contain at most 6 carbon atoms, these aryl, arylalkyl and arylalkenyl radicals being such that the aryl radical that they constitute or that they contain represents a monocyclic radical containing 5, 6 or 7 links or a radical constituted by condensed rings containing 8 to 14 links, these radicals containing optionally one or more heteroatoms chosen from oxygen, nitrogen and sulphur atoms, and being optionally substituted by one or more radicals chosen from halogen atoms, hydroxyl, nitro radicals, alkyl, alkenyl, haloalkyl, alkoxy and acyl radicals, these radicals containing at most 6 carbon atoms, amino radicals optionally substituted by one or two identical or different alkyl radicals containing at most 6 carbon atoms, free, salified or esterified carboxy radicals, tetrazolyl, aryl and arylalkyl radicals, the two latter radicals being optionally substituted by one or more radicals chosen from halogen atoms, hydroxyl, trifluoromethyl, nitro radicals, free, salified or esterified carboxy radicals and tetrazolyl radicals, a —$(CH_2)_{m1}$—$S(O)_{m2}$—X—$R_{10}$ radical as defined above, or $R_6$ and $R_7$ or $R_8$ and $R_9$ form respectively with the nitrogen atom to which they are linked a monocyclic radical containing 5, 6 or 7 links or a radical constituted by condensed rings containing 8 to 14 links, these identical or different radicals optionally containing one or more other heteroatoms chosen from oxygen, nitrogen and sulphur atoms, and being optionally substituted by one or more radicals chosen from halogen atoms, hydroxyl radicals, nitro, alkyl, alkenyl, haloalkyl, alkoxy and acyl radicals, these radicals containing at most 6 carbon atoms, amino radicals optionally substituted by one or two identical or different alkyl radicals containing at most 6 carbon atoms, free, salified or esterified carboxy radicals, tetrazolyl, aryl and arylalkyl radicals, these two latter radicals being optionally substituted by one or more radicals chosen from halogen atoms, hydroxyl radicals, trifluoromethyl, nitro radicals, free, salified or esterified carboxy radicals and tetrazolyl radicals, or $R_8$ and $R_9$, identical or different, represent an acyl radical or one of $R_8$ or $R_9$ represents a carbamoyl, alkoxycarbonyl or benzyloxycarbonyl radical or $R_8$ and $R_9$ form together with the nitrogen atom to which they are linked a phthalimido or succinimido radical, c) the —S—S—$R_{4B}$, radical in which $R_{4B}$, represents the values defined for $R_{4B}$ except for the amino and alkoxy radicals, it being understood that at least one of $R_{2B}$ and $R_{3B}$ represents the —$OR_{4B}$ radical or one of the radicals:

$$-S(O)_nR_{4B}, \quad -\underset{\underset{N-S(O)_n-X'}{\|}}{\overset{\overset{O}{\|}}{S}}-R_{4B} \quad \text{or} \quad -S-S-R_{4B'},$$

knowing that $R_{2B}$ and $R_{3B}$ cannot represent simultaneously the —S—S—$R_{4B}$' radical, m represents the value 0, 1 or 2, $Y_B$ represents the —$Y_{1B}$—B—$Y_{2B}$ radical in which:

$Y_{1B}$ represents a monocyclic aryl radical containing 5, 6 or 7 links or constituted by condensed rings containing 8 to 10 links, these radicals optionally containing one or more heteroatoms chosen from oxygen, nitrogen and sulphur atoms, and being optionally substituted by one or more radicals chosen from the radicals that can be represented by $R_{2B}$ and $R_{3B}$, B represents:

either a single bond between $Y_{1B}$ and $Y_{2B}$, or one of the following divalent radicals: —CO—, —O—, —NH—CO—, —CO—NH— or —O—$(CH_2)_p$— with p representing the values 1, 2 or 3, $Y_{2B}$ represents:

either, whatever the value of B and $Y_{2B}$ being identical or different to $Y_{1B}$, the values defined for $Y_{1B}$, or, if B represents a single bond, a hydrogen atom, a cyano radical, a free, salified or esterified carboxy radical, the said products of formula ($I_B$) being in all the possible racemic, enantiomeric and diastereoisomeric isomer forms, as well as the addition salts with mineral and organic acids or with mineral and organic bases of the said products of formula ($I_B$).

Also a subject of the present invention is the products of formula ($I_B$) as defined above and corresponding to formula

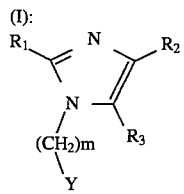

in which:

$R_1$ represents an alkyl, alkenyl, alkynyl, alkylthio radical, each of these radicals being linear or branched and containing at most 10 carbon atoms, or a cycloalkyl radical containing 3 to 7 carbon atoms, all these radicals being optionally substituted by one or more identical or different radicals chosen from halogen atoms, hydroxyl, alkoxy radicals containing at most 6 carbon atoms, alkylthio, acyl radicals, free, salified or esterified carboxy radicals, cyano, nitro, amino radicals optionally substituted by one or two identical or different alkyl radicals containing at most 6 carbon atoms, cycloalkyl radicals containing 3 to 7 carbon atoms and aryl radicals optionally substituted by one or more identical or different radicals chosen from halogen atoms, hydroxyl radicals, alkyl, alkenyl and alkoxy radicals containing at most 6 carbon atoms, haloalkyl, alkylthio, haloalkylthio, haloalkoxy, aryloxy, arylalkoxy, carbamoyl, acyl, acyloxy radicals, free, salified or esterified carboxy radicals, tetrazolyl, cyano, nitro, amino radicals optionally substituted by one or two identical or different alkyl radicals containing at most 6 carbon atoms and phenyl radicals optionally substituted by one or more radicals chosen from halogen atoms, hydroxyl radicals, alkyl and alkoxy radicals containing at most 4 carbon atoms, trifluoromethyl radicals, free, salified or esterified carboxy radicals and tetrazolyl radicals, $R_2$ and $R_3$, identical or different, are chosen from:

a) the hydrogen atom, the following radicals: mercapto, formyl, acyl, free, salified or esterified carboxy, nitro, cyano, or $-PO_3(R)_2$ in which R represents a hydrogen atom, an alkyl or aryl radical, b) the radicals $R_4$,

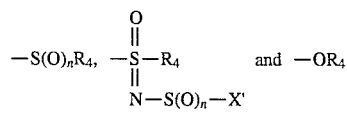

in which:

n represents the values 0, 1 or 2,

X' represents an aryl radical optionally substituted by one or more identical or different radicals chosen from halogen atoms, hydroxyl radicals, alkyl, alkenyl and alkoxy radicals containing at most 6 carbon atoms, haloalkyl, alkylthio, haloalkylthio, haloalkoxy, aryloxy, arylalkoxy, carbamoyl, acyl, acyloxy radicals, free, salified or esterified carboxy radicals tetrazolyl, cyano, nitro radicals, amino radicals optionally substituted by one or two identical or different alkyl radicals containing at most 6 carbon atoms and phenyl radicals optionally substituted by one or more radicals chosen from halogen atoms, hydroxyl radicals, alkyl and alkoxy radicals containing at most 4 carbon atoms, trifluoromethyl radicals, free, salified or esterified carboxy radicals and tetrazolyl radicals, $R_4$ represents a hydrogen atom an alkyl, alkenyl, alkynyl, or acyl radical, each of these radicals being linear or branched and containing at most 6 carbon atoms, an amino radical optionally substituted by one or two identical or different alkyl radicals containing at most 6 carbon atoms, a cycloalkyl radical containing 3 to 6 carbon atoms or an aryl radical, the alkyl, alkenyl, cycloalkyl and aryl radicals being optionally substituted by one or more identical or different radicals chosen from:

halogen atoms, hydroxyl, haloalkyl, alkylthio, mercapto, acylthio, haloalkylkhio, haloalkoxy, cyano, azido, nitro radicals, the $-O-Si-(R_5)_3$ or $-Si(R_5)_3$ radical in which $R_5$ represents an alkyl radical containing at most 4 carbon atoms, aryl, arylalkyl, arylalkenyl, arylkhio, aryloxy and arylalkoxy radicals in which, if appropriate, the alkyl, alkenyl and alkoxy radicals contain at most 6 carbon atoms and the aryl radical is optionally substituted by one or more identical or different radicals chosen from halogen atoms, hydroxyl radicals, alkyl, alkenyl and alkoxy radicals containing at most 6 carbon atoms, haloalkyl, alkylthio, haloalkylthio, haloalkoxy, aryloxy, arylalkoxy, carbamoyl, acyl, acyloxy radicals, free, salified or esterified carboxy radicals, tetrazolyl, cyano, nitro radicals, amino radicals optionally substituted by one or two identical or different alkyl radicals containing at most 6 carbon atoms and phenyl radicals optionally substituted by one or more radicals chosen from halogen atoms, hydroxyl radicals, alkyl and alkoxy radicals containing at most 4 carbon atoms, trifluoromethyl radicals, free, salified or esterified carboxy radicals and tetrazolyl radicals, alkyl, alkenyl and alkoxy radicals containing at most 6 carbon atoms, free, salified or esterified carboxy radicals, tetrazolyl, acyl, acyloxy radicals, $-SO_3H$ radicals, and the radicals

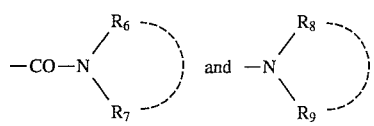

in which:

either $R_6$ and $R_7$ or $R_8$ and $R_9$, identical or different, are chosen from:

the hydrogen atom, alkyl and alkenyl radicals containing at most 6 carbon atoms and optionally substituted by one or more identical or different radicals chosen from halogen atoms, the hydroxyl radical or alkoxy radicals containing at most 6 carbon atoms, aryl, arylalkyl and arylalkenyl radicals in which the linear or branched alkyl and alkenyl radicals contain at most 6 carbon atoms, these aryl, arylalkyl and arylalkenyl radicals being such that the aryl radical that they constitute or that they contain represents a monocyclic radical containing 5, 6 or 7 links or a radical constituted by condensed rings containing 8 to 14 links, these radicals optionally containing one or more heteroatoms chosen from oxygen, nitrogen and sulphur atoms, and being optionally substituted by one or more radicals chosen from halogen atoms, hydroxyl, nitro radicals, alkyl, alkenyl, haloalkyl, alkoxy and acyl radicals, these radicals containing at most 6 carbon atoms, amino radicals optionally substituted by one or two identical or different alkyl radicals containing at most 6 carbon atoms, free, salified or esterified carboxy radicals, tetrazolyl radicals, aryl and arylalkyl radicals, these two latter radicals being optionally substituted by one or more radicals chosen from halogen atoms, hydroxyl radicals, trifluoromethyl, nitro radicals, free, salified or esterified carboxy radicals and tetrazolyl radicals, or $R_6$ and $R_7$ or $R_8$ and $R_9$ form respectively with the nitrogen atom to which they are linked a monocyclic radical containing 5, 6 or 7 links or a radical constituted by condensed rings containing 8 to 14 links, these identical or different radicals optionally containing one or more other heteroatoms chosen from oxygen, nitrogen and sulphur atoms, and being optionally substituted by one or more radicals chosen from halogen atoms, hydroxyl, nitro radicals, alkyl, alkenyl, haloalkyl, alkoxy and acyl radicals, these radicals containing at most 6 carbon atoms, amino radicals optionally substituted by one or two identical or different alkyl radicals containing at most 6 carbon atoms, free, salified or esterified carboxy radicals, tetrazolyl radicals, aryl and arylalkyl radicals, these two latter radicals being optionally substituted by one or more radicals chosen from halogen atoms, hydroxyl radicals, trifluoromethyl, nitro radicals, free, salified or esterified carboxy radicals and tetrazolyl radicals, or $R_8$ and $R_9$, identical or different, represent an acyl radical or one of $R_8$ or $R_9$ represents a carbamoyl, alkoxycarbonyl or benzyloxycarbonyl radical or $R_8$ and $R_9$ form together with the nitrogen atom to which they are linked a phthalimido or succinimido radical,, c) the —S—S—$R_4$, radical in which $R_4$, represents the values defined for $R_4$ except for the amino and alkoxy radicals, m represents the value 0, 1 or 2, Y represents the —$Y_1$—B—$Y_2$ radical in which:

$Y_1$ represents a monocyclic aryl radical containing 5, 6 or 7 links or constituted by condensed rings containing 8 to 10 links, these radicals optionally containing one or more heteroatoms chosen from oxygen, nitrogen and sulphur atoms, and being optionally substituted by one or more radicals chosen from the radicals that can be represented by $R_2$ and $R_3$, B represents:
either a single bond between $Y_1$ and $Y_2$,
or one of the following divalent radicals: —CO—, —O—, —NH—CO—, —CO—NH— or —O—$(CH_2)_p$— with p representing the values 1, 2 for 3, $Y_2$ represents:
either, whatever the value of B and $Y_2$ being identical or different to $Y_1$, the values defined for $Y_1$,
or, if B represents a single bond, a hydrogen atom, a cyano radical, a free, salified or esterified carboxy radical, it being understood that at least one of $R_2$ and $R_3$ represents one of the radicals:

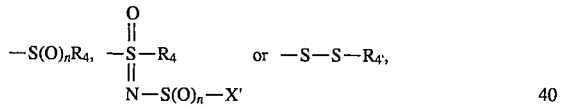

knowing that $R_2$ and $R_3$ cannot represent simultaneously the —S—S—$R_4$' radical, the said products of formula (I) being in all the possible racemic, enantiomeric and diastereoisomeric isomer forms, as well as the addition salts with mineral and organic acids or with mineral and organic bases of the said products of formula (I).

In the products of formulae ($I_B$) and (I) and in what follows:

the term linear or branched alkyl radical preferably designates methyl, ethyl, propyl, isopropyl, butyl, isobutyl, sec-butyl and tert-butyl radicals but can also represent a pentyl or hexyl radical and in particular an isopentyl and isohexyl radical, the term linear or branched alkenyl radical preferably designates a vinyl, allyl, 1-propenyl, butenyl radical and particularly 1-butenyl or pentenyl radical, the term linear or branched alkynyl radical preferably designates an ethynyl, propargyl, butynyl or pentynyl radical.

Among the alkyl radicals interrupted by one or more heteroatoms, there can be mentioned methoxymethyl, methoxyethoxymethyl, propylthiopropyl, propyloxypropyl, propylthioethyl, methylthiomethyl radicals, the term halogen atom preferably designates a chlorine atom, but can also represent a fluorine, bromine or iodine atom, the term linear or branched alkoxy radical preferably designates methoxy, ethoxy, propoxy or isopropoxy radicals, but can also represent a linear, secondary or tertiary butoxy radical, the term acyl radical preferably designates a radical having 1 to 6 carbon atoms such as for example the formyl, acetyl, propionyl, butyryl or benzoyl radical, but also the pentanoyl, hexanoyl, acryloyl, crotonoyl or carbamoyl radical, the term amino substituted by one or two alkyl radicals preferably designates radicals in which the alkyl radical or radicals are chosen from alkyl radicals as defined above such as for example for monoalkylamino in methylamino or ethylamino, or for example for dialkylamino in dimethylamino or also methylethylamino, the term acyloxy radical designates for example a radical in which the acyl radical has the values indicated above and preferably designates a formyloxy, acetyloxy, propionyloxy, butyryloxy or benzoyloxy radical, the term cycloalkyl radical preferably designates cyclopropyl, cyclobutyl, cyclopentyl or cyclohexyl radicals.

the terms monocyclic radical and radical constituted by condensed rings designate saturated or unsaturated carbocyclic or heterocyclic radicals, it being understood that the heterocyclic radicals as defined above can contain one or more heteroatoms chosen from oxygen, nitrogen or sulphur atoms and that when these heterocyclic radicals contain more than one heteroatom, the heteroatoms of these heterocyclic radicals can be identical or different:

the term monocyciic radical p eferabiy designates the radicals which contain 5 to 7 links: among the saturated carbocyclic monocyclic radicals there can be mentioned, for example, cyclohexyl and cyclopentyl radicals; among the unsaturated carbocyclic monocyclic radicals there can be mentioned, for example, cyclopentenyl, cyclohexenyl, cyclopentadienyl, cyclohexadienyl radicals and the carbocyclic aryl radicals such as the phenyl radical; among the saturated heterocyclic monocyclic radicals there can be mentioned for example pyrrolidinyl, imidazolidinyl, pyrazolidinyl, piperidyl, piperazinyl, morpholinyl, thiomorpholinyl, and azepinyl radicals, among the unsaturated heterocyclic monocyclic radicals there can be mentioned, for example, thienyl, furyl, pyrannyl, pyrrolyl, imidazolyl, pyrazolyl, pyridyl, pyrazinyl, pyrimidinyl, pyridazinyl, thiazolyl, thiadiazolyl, oxazolyl, furazannyl, and pyrrolinyl radicals such as delta 2-pyrrolinyl, imidazolinyl such a delta 2-imidazolinyl, pyrazolinyl such as delta 3-pyrazolinyl, as well as the isomers of position of the heteroatom or heteroatoms that can be contained by these radicals such as, for example, isothiazolyl or isoxazolyl radicals, the term radical constituted by condensed rings preferably designates radicals which contain 8 to 14 links: among the radicals constituted by saturated carbocyclic condensed rings there can be mentioned, for example, indanyl bicyclo-[4,4,0]decyl or bicyclo[4,4,1]undecyl radicals; among the radicals constituted by unsaturated carbocyclic condensed rings there can be mentioned aryl radicals, for example, naphthyl or phenanthryl, indenyl radicals; among the radicals constituted by saturated heterocyclic condensed rings there can be mentioned, for example, 1-oxa-spiro[4,5]decyl, tetrahydropyrane-2-spirocyclohexyl, cyclohexanespiro-2'-(tetrahydrofuran) or 1,10-diaza-anthr-4-yl, among the radicals constituted by unsaturated heterocyclic condensed rings there canbe mentioned aryl radicals such as, for example, benzothienyl, naphtho[2,3-b] thienyl, indenyl, thianthrenyl, isobenzofurannyl, chromenyl, xanthenyl, phenoxathiinyl, indolizinyl, isoindolyl, 3H-indolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, beta-carbolinyl, acridinyl, phenazinyl, phenothiazinyl, phenoxazinyl, indolinyl, isoindolinyl or also condensed polycyclic systems constituted by heterocyclic monocyclics as defined above, for example, such as for example furo-[2,3-b]-pyrrole or thieno-[2,3-b]-furane, the term aryl radical designates carbocyclic or heterocyclic unsaturated radicals, monocyclic or constituted by condensed rings, it being understood that the heterocyclic radicals can contain one or more heteroatoms chosen from oxygen, nitrogen or sulphur atoms and that when these heterocyclic radicals contain more than one heteroatom, the heteroatoms of these heterocyclic radicals can be identical or different: thus, these radicals that are designated by the term aryl radical can be chosen from the radicals as defined above.

As examples of such aryl radicals, there can be mentioned the following radicals: phenyl, naphthyl, thienyl such as 2-thienyl and 3-thienyl, furyl such as 2-furyl, pyridyl such as 3-pyridyl, pyrimidyl, pyrrolyl, thiazolyl, isothiazolyl, diazolyl, triazolyl, tetrazolyl, thiadiazolyl, thiatriazolyl, oxazolyl, oxadiazolyl, 3- or 4-isoxazolyl; condensed heterocyclic groups containing at least one heteroatom chosen from sulphur, nitrogen and oxygen, for example benzothienyl such as 3-benzothienyl, benzofuryl, benzopyrrolyl, benzimidazolyl, benzoxazolyl, thionaphthyl, indolyl or purinyl.

the terms arylalkyl and arylalkenyl designate radicals in which the alkyl, alkenyl and aryl radicals respectively can take the values defined above for these radicals; as examples of such arylalkyl radicals there can be mentioned the following radicals: benzyl, diphenylmethyl, triphenylmethyl, naphthylmethyl, indenylmethyl, thienylmethyl such as 2-thienylmethyl, furylmethyl such as furfuryl, pyridylmethyl, pyrimidylmethyl or pyrrolylmethyl, it being understood that in the non-exhaustive list of examples of radicals as mentioned above, the alkyl radical can be represented quite as equally by ethyl, propyl or butyl radicals such as, for example, in the phenylethyl radical;

as examples of arylalkenyl radicals, there can be mentioned the examples given above of arylalkyl radicals in which the alkyl radical is replaced by an alkenyl radical such as for example in phenylvinyl or phenylallyl radicals, it being understood that in these radicals the phenyl radical can be replaced quite as equally by a naphthyl or pyridyl radical or also for example one of the aryl radicals as defined above in the non-exhaustive list of aralkyl radicals, the term haloalkyl radical preferably designates radicals in which the alkyl radical is as defined above and is substituted by one or more halogen atoms as defined above such as for example in bromoethyl, trifluoromethyl, trifluoroethyl or also pentafluoroethyl, the term alkylthio radical preferably designates radicals in which the alkyl radical is as defined above such as for example in methylthio or ethylthio, the term haloalkylthio radical preferably designates radicals in which the alkyl radical is as defined above and is substituted by one or more halogen atoms as defined above such as for example in bromoethylthio, trifluoromethylthio, trifluoroethylthio or also pentafluoroethylthio, the term haloalkoxy radical preferably designates radicals in which the alkoxy radical is as defined above and is substituted by one or more halogen atoms as defined above such as for example in bromoethoxy, trifluoromethoxy, trifluoroethoxy or also pentafluoroethoxy, the term aryloxy radical preferably designates radicals in which the aryl radical is as defined above such as for example in phenoxy, the term arylalkoxy radical preferably designates radicals in which the aryl radical and the alkoxy radical represent radicals as defined above such as for example in benzyloxy, phenylethoxy or phenylisopropoxy, the term carbamoyl radical also designates substituted carbamoyl radicals, for example a carbamoyl lower N-monoalkyl group, such as N-methylcarbamoyl, N-ethylcarbamoyl, a lower N,N-dialkyl carbamoyl group, such as N,N-dimethylcarbamoyl, N,N-diethylcarbamoyl; an N-(lower hydroxyalkyl) carbamoyl group, such as N-(hydroxymethyl) carbamoyl, N-(hydroxyethyl) carbamoyl, a lower carbamoylalkyl group, such as carbamoylmethyl, carbamoylethyl, the term acyloxy radical designates radicals in which the acyl radicals have the meaning indicated above and for example preferably acetoxy or propionyloxy radicals, the term arylthio radical preferably designates radicals in which the aryl radical represents radicals as defined above such as for example in phenylthio, the term aryl radical substituted by an alkylthio radical represents for example the benzylthio radical.

In the products of formulae ($I_B$) and (I) and in what follows, the alkyl, alkenyl, alkynyl, cycloalkyl and aryl radicals:

that can be represented by $R_2$ and $R_3$, that can be contained by the radical —$S(O)_n R_4$ that can be represented by $R_2$ and $R_3$, or - that can be carried by $R_2$ and $R_3$, can take the values defined above for these radicals which can be or cannot be substituted by one or more identical or different substituents as defined above for these radicals. $R_2$ and $R_3$ can thus, for example, represent an alkylthio, arylthio, alkylsulphinyl, arylsulphinyl, alkylsulphonyl or arylsulphonyl radical but also a cycloalkylthio radical such as for example cyclohexylthio:

the terms alkylthio, alkylsulphinyl and alkylsulphonyl radical designate radicals in which the linear or branched alkyl radical can represent, for example, the values indicated above for the alkyl radical; thus these radicals preferably represent methylthio, hydroxymethylthio, ethylthio, aminoethylthio, methylsulphinyl, ethylsulphinyl, methylsulphonyl, ethylsulphonyl radicals but can also represent a propylthio, isopropylthio, butylthio, sec-butylthio, tert-butylthio, isopentylthio or isohexylthio or those radicals in which the thio radical is oxidized into a sulphinyl or sulphonyl radical, the term arylthio, arylsulphinyl and arylsulphonyl radical designates radicals in which the aryl radical can represent, for example, the values indicated above for the aryl radical such as, for example, in phenylthio, pyridylthio or pyrimidylthio, imidazolylthio, N-methylimidazolylthio or those radicals in which the thio radical is oxidized into a sulphinyl or sulphonyl radical such as for example in phenylsulphinyl or phenylsulphonyl.

As examples of alkyl radicals substituted by an aryl radical, there can be mentioned, for example, the following radicals: benzyl, diphenylmethyl, triphenylmethyl, naphthylmethyl, indenylmethyl, thienylmethyl such as 2-thienylmethyl, furylmethyl such as furfuryl, pyridylmethyl, pyrimidylmethyl or pyrrolylmethyl, it being understood that in the non-exhaustive list of examples of radicals as mentioned above, the alkyl radical can be represented quite as equally by ethyl, propyl or butyl radicals such as, for example, in the phenethyl radical.

As examples of alkenyl radicals substituted by an aryl radical, there can be mentioned, for example, the examples given above of arylalkyl radicals in which the alkyl radical is replaced by an alkenyl radical such as for example in phenylvinyl or phenylallyl radicals, it being understood that in these radicals the phenyl radical can be replaced quite as equally by a naphthyl or pyridyl radical or also for example one of the aryl radicals as defined above.

The carbocyclic or heterocyclic radicals as defined above preferably designate phenyl, benzyl, phenethyl, naphthyl, indolyl, indolinyl, thienyl, furyl, pyrrolyl, pyridyl, pyrrolidinyl, piperidino, morpholino, piperazinyl, these radicals being able to be substituted by one or more radicals as defined above such as for example in methylpiperazinyl, fluoromethylpiperazinyl, ethylpiperazinyl, propylpiperazinyl, phenylpiperazinyl or benzylpiperazinyl.

The carbamoyl and amino radicals that can be represented by or carried by one or more of the optional substituents of the radicals defined in the products of formulae ($I_B$) and (I) and in what follows and that can be represented, in particular, by: the radicals

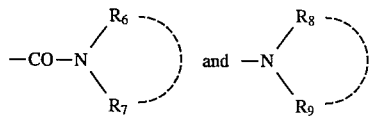

designate radicals in which two identical or different radicals are linked to the nitrogen atom, chosen from the hydrogen atom to give the amino radical; alkyl radicals as defined above to give preferably monoalkyl- or dialkylamino radicals in which the linear or branched alkyl radicals contain 1 to 6 carbon atoms and in particular methyl, ethyl, isopropyl, methoxymethyl, methoxyethyl, ethoxyethyl radicals; carboxyclic or heterocyclic radicals that can be represented by $R_6$, $R_7$, $R_8$ and $R_9$ can take the values defined above for these radicals and in particular phenyl, benzyl, phenethyl, naphthyl, indolyl, indolinyl, thienyl, furyl, pyrrolyl, pyridyl, pyrrolidinyl, piperidino, morpholino, piperazinyl, these radicals being able to be substituted by one or more radicals as defined above such as for example in methylpiperazinyl, fluoromethylpiperazinyl, ethylpiperazinyl, propylpiperazinyl, phenylpiperazinyl or benzylpiperazinyl.

The expression amino acid preferably designates a derivative remainder of one of the natural amino acids such as glycine, alanine, valine or one of the other natural amino acids known to a man skilled in the art.

When $R_6$ and $R_7$ on the one hand or $R_8$ and $R_9$ on the other hand form, together with the nitrogen atom to which they are linked, a heterocycle, it is, for example, one of the following rings: pyrrolyl, imidazolyl, pyrazinyl, indolyl, indolinyl, purinyl, pyrrolidinyl, piperidyl, piperidino, morpholino, piperazinyl, imidazolidinyl, pyrazolidinyl, thiomorpholinyl, azepine; these radicals can be optionally substituted by the substituents already mentioned previously and in particular by one or more radicals chosen from chlorine and fluorine atoms, methyl, ethyl, isopropyl, tertbutyl, methoxy, ethoxy, propoxy, benzoyl, methoxycarbonyl, ethoxycarbonyl, such as for example in methylpiperazinyl, ethylpiperazinyl, propylpiperazinyl, phenylpiperazinyl or benzylpiperazinyl: in these two latter radicals, the phenyl and benzyl radicals can be substituted as indicated previously in the aryl, arylalkyl and arylalkenyl radicals, such as for example in chlorophenyl or trifluorophenyl.

The heterocycle that can be formed by $R_6$ and $R_7$ on the one hand or $R_8$ and $R_9$ on the other hand respectively, with the nitrogen atom to which they are linked, preferably represents a saturated heterocycle.

The acyl radicals that can be represented by $R_8$ and $R_9$ are as defined previously and can be chosen for example from acetyl, propionyl, butyryl, pentanoyl or carbamoyl radicals.

In the case where one or both of $R_2$ and $R_3$, identical or different, contain a carbamoyl or amino radical, that is:

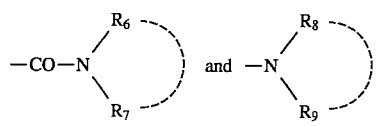

$R_6$, $R_7$, $R_8$ and $R_9$, identical or different, can represent all four of the aliphatic or cyclized chains or one or both of $R_6$ and $R_7$ on the one hand and $R_8$ and $R_9$ on the other hand can form, with the nitrogen atom to which they are linked, a heterocycle as defined above. The substituted carbamoyl

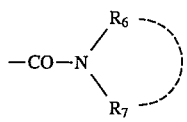

and substituted amino

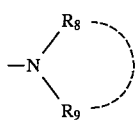

radicals designate respectively the radicals in which the nitrogen atom can be substituted by one or two radicals chosen from the radicals as defined previously: by way of example in a non-exhaustive manner, there can be mentioned as a substituted carbamoyl radical the lower N-monoalkyl carbamoyl group, for example, N-methylcarbamoyl, N-ethylcarbamoyl; the lower N,N-dialkyl carbamoyl group, for example, N,N-dimethylcarbamoyl, N,N-diethylcarbamoyl; the N-(lower hydroxyalkyl) carbamoyl group, for example, N-(hydroxymethyl) carbamoyl, N-(hydroxyethyl) carbamoyl; the lower carbamoylalkyl group, for example carbamoylmethyl, carbamoylethyl; phenylcarbamoyl; pyridylcarbamoyl; benzylcarbamoyl; N-methyl N-phenylcarbamoyl; pyridylmethylcarbamoyl.

The substituted amino radical can be for example a monoalkyl- or dialkylamino radical in which the alkyl radical is chosen from methyl, ethyl or isopropyl radicals.

Examples of such a substituted amino radical are given in the experimental part hereafter.

When $R_8$ or $R_9$ represents an alkoxycarbonyl radical, this radical is preferably the tert-butyloxycarbonyl radical or the benzyloxycarbonyl radical.

According to whether m represents the value 0, 1 or 2, the —$(CH_2)_m$— radical represents a single bond, a methylene radical or an ethylene radical.

The radicals $Y_1$ and $Y_2$ can represent the values defined above for the aryl radicals, monocyclic or constituted by condensed rings, it being understood that in the case where B represents a single bond $Y_2$ can also represent a hydrogen atom, a cyano radical or a free, salified or esterified carboxy radical.

The radicals $Y_1$ or $Y_2$, identical or different, represent an aryl radical optionally substituted by one or more radicals preferably chosen from halogen atoms and the following radicals: hydroxyl, nitro, tetrazolyl, free, salified or esterified carboxy, alkyl, alkenyl, alkoxy and acyl, these radicals being as defined above.

Among the preferred products of formula (I) are the products in which $Y_1$ is not substituted and $Y_2$ is substituted by a free or esterified carboxy radical or by a tetrazolyl radical.

The carboxy radical or radicals of the products of formula (I) can be salified or esterified by various groups known to a man skilled in the art, amongst which there can be mentioned, for example:

among the salification compounds, mineral bases such as, for example, an equivalent of sodium, potassium, lithium, calcium, magnesium or ammonium or organic bases such as, for example, methylamine, propylamine, trimethylamine, diethylamine, triethylamine, N,N-dimethylethanolamine, tris (hydroxymethyl) amino methane, ethaholamine, pyridine, picoline, dicyclohexylamine, morpholine, benzylamine, procaine, lysine, arginine, histidine, N-methylglucamine, among the esterification compounds, alkyl radicals in order to form alkoxy carbonyl groups such as, for example, methoxycarbonyl, ethoxycarbonyl, tert-butoxycarbonyl or benzyloxycarbonyl, these alkyl radicals being able to be substituted by radicals chosen for example from halogen atoms, hydroxyl, alkoxy, acyl, acyloxy, alkylthio, amino or aryl radicals such as, for example, in the chloromethyl, hydroxypropyl, methoxymethyl, propionyloxymethyl, methylthiomethyl, dimethylaminoethyl, benzyl or phenethyl groups.

The addition salts with mineral or organic acids of the products of formula (I) can be, for example, the salts formed with the following acids: hydrochloric, hydrobromic, hydroiodic, nitric, sulphuric, phosphoric, propionic, acetic, formic, benzoic, maleic, fumaric, succinic, tartaric, citric, oxalic, glyoxylic, aspartic, ascorbic, alkylmonosulphonic such as for example methanesulphonic, ethanesulphonic, propanesulphonic, alkyldisulphonic such as for example methanedisulphonic, alpha, beta-ethanedisulphonic, arylmonosulphonic such as benzenesulphonic and aryldisulphonic.

When $R_2$ and $R_3$ both represent a sulphurous group of formula $-S(O)_nR_4$, $R_2$ and $R_3$ being identical or difference, the preferred products of the invention are in particular the products of formula (I) in which these sulphurous groups have the same degree of oxidation.

Among the preferred products of the invention there are in particular the products of formula (I) in which one of $R_2$ and $R_3$ represents a sulphurous group optionally oxidized as defined above by $-S(O)nR_4$ and the other one of $R_2$ and $R_3$ represents an $R_4$ radical as defined above and preferably an alkyl, alkenyl or aryl radical optionally substituted by one or more substituents as defined above.

Among the preferred products of the invention, there are quite particularly the products of formula (I) in which $R_2$ represents a sulphurous radical.

In the case where $R_2$ or $R_3$ represents an $-S(O)_nR_4$ radical and $R_4$ represents an amino radical, n is preferably equal to 2.

$R_{2B}$ and $R_{3B}$ can notably represent alkylthio, alkanylthio or alkynylthio radicals, optionally substituted by one or more radicals chosen from the following radicals: formyl; hydroxyl; alkoxy; acyloxy; free, salified or esterified carboxy; amino; substituted amino; carbamoyl; substituted carbamoyl; mercapto; alkylthio; acylthio such as acetylthio; arylthio such as phenylthio; sulpho, cycloalkyl such as cyclohexyl; pyridinyl; pyrimidinyl; phenyl.

Among the substituents that can be carried by the radicals $R_{2B}$ and $R_{3B}$, khe amino and carbamoyl radicals can notably be substituted by one or two radicals chosen from alkyl radicals and amino acids chosen from the 20 natural amino acids such as notably proline or for example glycine, alanine, leucine, isoleucine, valine or phenylalanine.

The amino and carbamoyl radicals that can be carried by the radicals $R_{2B}$ and $R_{3B}$ can also constitute derivatives cyclized by the formation of a cyclic radical between the nitrogen atom and its substituents as indicated above and hereafter.

$R_{2B}$ and $R_{3B}$ can thus notably represent alkylthio radicals, substituted by one or more halogen atoms such as chlorine and fluorine, such as for example the radicals: $-S-CF_3$; $-S-CHF_2$; $-S-CH_2F$; $-S-CF_2-CHF_2$; $-S-CF_2-CHFCl$.

The radicals $R_{2B}$ and $R_{3B}$ can thus represent the following radicals in which m, m1 and m2, identical or different, represent the values 0 to 6,

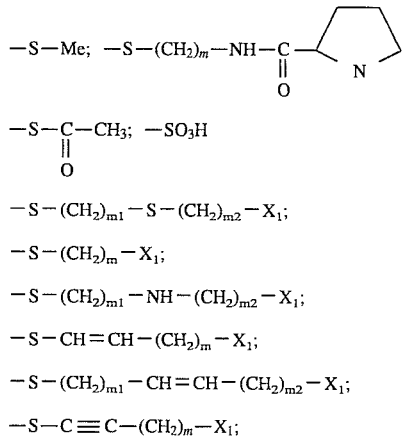

in which $X_1$ represents H, OH, cyclohexyl, pyridyl, pyrimidyl, phenyl, naphthyl, CHO, COOH, $NH_2$ or

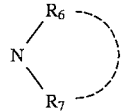

The radicals $R_{2B}$ and $R_{3B}$ can also represent, particularly, the following radicals:

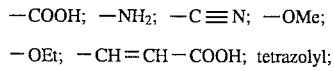

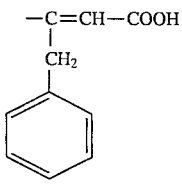

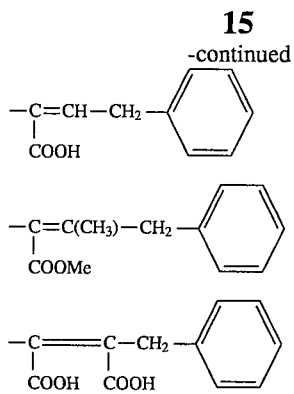

in all their isomer and cis-trans isomer forms.

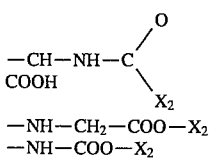
—NH—CH$_2$—COO—X$_2$
—NH—COO—X$_2$

X$_2$ representing an alkyl or aryl radical.

The radicals R$_{2B}$ and R$_{3B}$ can quite particularly represent the radical:

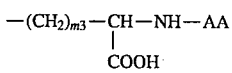

in which m3 represents the values 0 to 4 and AA represents a natural amino acid natural such as notably proline or glycine and the radical:

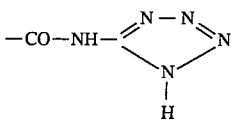

The products of formula (I$_B$) therefore represent particularly the products in which R$_{2B}$ and R$_{3B}$ have the meanings indicated above and quite particularly the products in which R$_{2B}$ represents an optionally substituted alkylthio radical as defined above or an alkoxy radical such as for example mekhoxy and R$_{3B}$ represents a free, salified or esterified, or amidified carboxy radical, such as notably —COOH, —COO methyl, —CONH$_2$ or

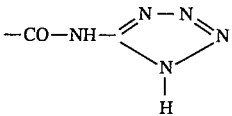

With these meanings indicated above for R$_{2B}$ and R$_{3B}$ in the products of formula (I$_B$) are associated the values indicated above for Y$_B$ and notably the biphenyl radical substituted in the ortho position by a formyl, free, salified or esterified carboxy, cyano, or optionally substituted tetrazolyl radical or the —(CH$_2$)$_{m1}$—SO$_2$—X—R$_{10}$ radical as defined above and notably the radicals indicated below:

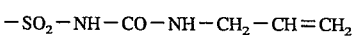

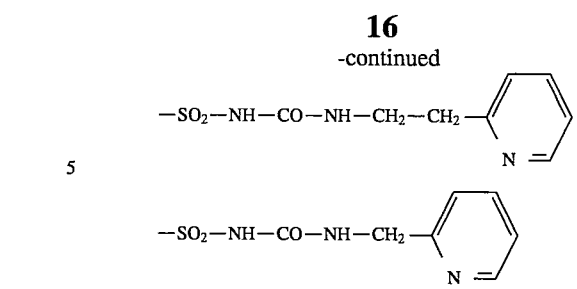

Notably a subject of the invention is the products of formula (I$_B$) as defined above and corresponding to the formula (I$_C$):

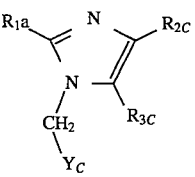

in which:

R$_{1a}$ represents a linear or branched alkyl or alkenyl radical containing at most 4 carbon atoms, R$_{2C}$ and R$_{3C}$, identical or different, are chosen from:

a) the hydrogen atom; the mercapto radical; formyl radicals; free, salified or esterified carboxy radicals; halogen atoms; the hydroxyl radical; alkoxy radicals containing at most 6 carbon atoms; cyano; nitro; benzoyl; acyl radicals;

b) the radicals R$_{4C}$, —S(O)$_n$R$_{4C}$ such that n represents the value 0, 1 or 2, and —OR$_{4C}$, in which R$_{4C}$ represents a linear or branched alkyl or alkenyl radical containing at most 6 carbon atoms, a cyclohexyl radical, a phenyl, pyridyl, pyrimidinyl or imidazolyl radical, all these radicals being optionally substituted by one or more identical or different radicals chosen from:

halogen atoms, hydroxyl, mercapto, acylthio, trifluoromethyl, trifluoromethylthio, trifluoromethoxy, cyano, azido, nitro, formyl, sulpho radicals, phenyl, phenylthio, cycloalkyl, alkyl, alkylthio and alkoxy radicals containing at most 6 carbon atoms, these radicals being themselves optionally substituted by one or more radicals chosen from halogen atoms, the hydroxyl radical, alkoxy radicals containing at most 4 carbon atoms, phenyl and free, salified or esterified carboxy radicals, free, salified or esterified carboxy radicals, acyl, acyloxy radicals, isoxazolyl, pyrrolidinyl, pyrrolidinylcarbonyl pyridyl, pyrimidyl, thiazolyl, diazolyl, piperidinyl, tetrazolyl, tetrahydrofurannyl, all these radicals being optionally substituted by a methyl, ethyl or nitro radical, the radicals

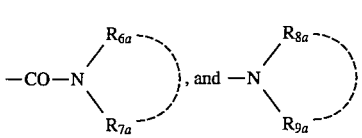

in which:

either R$_{6a}$, R$_{7a}$, R$_{8a}$ and R$_{9a}$, identical or different, are chosen from the hydrogen atom, the hydroxyl radical, amino acids, alkyl, alkoxy, acyloxy or acyl radicals, these radicals containing at most 6 carbon atoms, free, salified or esterified carboxy radicals, phenyl, benzyl, phenethyl, azepine, piperidyl, morpholine, pyrrolidinyl, piperazinyl radicals, or on the one hand $R_{6a}$ and $R_{7a}$ and on the other hand $R_{8a}$ and $R_{9a}$ form respectively with the nitrogen atom to which they are linked, a heterocyclic radical, these identical or different radicals being chosen from the following radicals: imidazolyl, pyrrolyl, pyrrolinyl, pyrrolidinyl, pyridyl, piperidinyl, pyrimidinyl, pyridazinyl, pyrazinyl, piperazinyl, phenylpiperazinyl, piperidyl, oxazolyl, morpholinyl and thiomorpholinyl, azepine, indolyl, these radicals being optionally substituted by one or more identical or different radicals chosen from halogen atoms, hydroxyl radicals, nitro, cyano, acyl, trifluoromethyl, alkyl and alkoxy radicals, these radicals containing at most 6. carbon atoms, free, salified or esterified carboxy radicals, tetrazolyl, phenyl and oxazolyl radicals, $Y_C$ represents the —$Y_{1C}$—Ba—$Y_{2C}$ radical in which:

$Y_{1C}$ represents a phenyl radical, $B_a$ represents a single bond or the —CO—NH— radical, $Y_{2C}$ is such that:

either, if $B_a$ represents a single bond or a —CO—NH— radical, $Y_{2C}$ represents a phenyl radical optionally substituted by one or more radicals chosen from free, salified or esterified carboxy radicals, the cyano radical, the tetrazolyl radical and the —$(CH_2)_p$—$SO_2$—$XC$—$R_{10C}$ radical in which p represents the values 0 and 1, $X_C$ represents the radicals —NH—, —NH—CO—, —NH—CO—NH— or a single bond and $R_{10C}$ represents one of the following radicals: methyl, ethyl, propyl, vinyl, allyl, pyridyl, phenyl, benzyl, pyridylmethyl, pyridylethyl, pyrimidyl, tetrazolyl, thiazolyl, diazolyl, piperidinyl or tetrahydrofurannyl, all these radicals being optionally substituted by one cr more substituents chosen from halogen atoms, hydroxyl, alkyl and alkoxy radicals containing at most 4 carbon atoms, trifluoromethyl and nitro radicals, or, if $B_a$ represents a single bond, $Y_{2C}$ represents a cyano radical or free, salified or esterified carboxy radical or a tetrazolyl radical, the said products of formula ($I_C$) being in all the possible racemic, enantiomeric and diastereoisomeric isomer forms, as well as the addition salts with mineral and organic acids or with mineral and organic bases of the said products of formula ($I_C$).

A particular subject of the invention is the products of formula ($I_B$) as defined above, in which:

$R_1$ represents an alkyl radical containing at most 4 carbon atoms, $R_{2B}$ and $R_{3B}$, identical or different, are chosen from:

a hydrogen atom, a carboxy radical free, salified or esterified by an alkyl radical, formyl, acyloxy, sulpho, optionally substituted alkyl and alkoxy, phenylthio phenylsulphonyl phenylsulphinyl alkylthio, alkylsulphonyl and alkylsulphinyl, optionally substituted, as in all those radicals that can be represented by $R_{2B}$ and $R_{3B}$, the alkyl and alkoxy radicals contain at most 6 carbon atoms, and the alkyl, alkoxy and phenyl radicals are optionally substituted by one or more radicals chosen from halogen atoms and hydroxyl radicals, trifluoromethyl, acyloxy, free, salified or esterified carboxy, phenyl, pyridyl, tetrazolyl, alkyl and alkoxy containing at most 4 carbon atoms and themselves optionally substituted by an alkoxy radical containing at most 4 carbon atoms, and $Y_B$ represents the —$Y_{1B}$—B—$Y_{2B}$ radical in which YIB represents a phenyt radical, B represents a single carbon-carbon bond and $Y_{2B}$ represents a carboxy radical, free or esterified by a linear or branched alkyl radical containing at most 4 carbon atoms or a phenyl radical optionally substituted by a carboxy radical free or esterified by a linear or branched alkyl radical containing at most 4 carbon atoms, a cyano radical or an optionally salified tetrazolyl radical, the said products of formula ($I_B$) being in all the possible racemic, enantiomeric and diastereoisomeric isomer forms, as well as the addition salts with mineral and organic acids or with mineral and organic bases of the said products of formula ($I_B$).

A more particular subject of the invention is the products of formula ($I_B$) as defined above and corresponding to the formula ($I_a$):

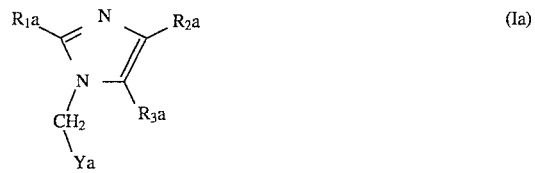
(Ia)

in which:

$R_{1a}$ represents a linear or branched alkyl or alkenyl radical containing at most 4 carbon atoms, $R_{2a}$ and $R_{3a}$, identical or different, are chosen from:

a) the hydrogen atom, the mcrcapto radical, the formyl radical, the free, salified or esterified carboxy radical, b) the radicals $R_4$a and —$S(O)_nR_{4a}$ such that n represents the value 0, 1 or 2, in which $R_4$a represents a linear or branched alkyl or alkenyl radical containing at most 4 carbon atoms, a cyclohexyl radical, a phenyl, pyridyl, pyrimidinyl or imidazolyl radical, all these radicals being optionally substituted by one or more identical or different radicals chosen from:

halogen atoms, hydroxyl, mercapto, acylthio, trifluoromethyl, trifluoromethylthio, trifluoromethoxy, cyano, azido, or nitro radicals, the phenyl radical, alkyl and alkoxy radicals containing at most 4 carbon atoms, free, salified or esterified carboxy radicals, tetrazolyl, acyl, acyloxy radicals, and the radicals

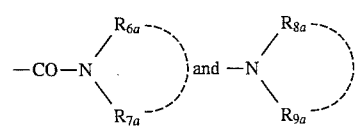

in which:

either $R_{6a}$, $R_{7a}$, $R_{8a}$ and $R_{9a}$, identical or different, are chosen from the hydrogen atom, the hydroxyl radical, alkyl, alkoxy, acyloxy or acyl radicals, these radicals containing at most 6 carbon atoms, free, salified or esterified carboxy radicals, phenyl, benzyl, phenethyl, azepine, piperidyl, morpholine, pyrrolidinyl, or piperazinyl radicals, or on the one hand $R_{6a}$ and $R_{7a}$ and on the other hand $R_{8a}$ and $R_{9a}$ form respectively, with the nitrogen atom to which they are linked, a radical, these identical or different radicals being chosen from the following radicals: imidazolyl, pyrrolyl, pyrrolinyl, pyrrolidinyl, pyridyl, piperidinyl, pyrimidinyl, pyridazinyl, pyrazinyl, piperazinyl, phenylpiperazinyl, piperidyl, oxazolyl, morpholinyl and thiomorpholinyl, azepine, indolyl, these radicals being optionally substituted by one or more identical or different radicals chosen from halogen atoms, hydroxyl, trifluoromethyl, alkyl and alkoxy radicals, these radicals containing at most 6 carbon atoms, it being understood that at least one of $R_{2a}$ or $R_{3a}$ represents the —S(O)n$R_4$a radical, $Y_a$ represents the —Y1a-Ba—$Y_{2a}$ radical in which:

$Y_{1a}$ represents a phenyl radical, $B_a$ represents a single bond or the —CO—NH— radical, $Y_{2a}$ is such that:

either, if $B_a$ represents a single bond or a —CO—NH— radical, $Y_{2a}$ represents a phenyl radical substituted in the ortho position by a free, salified or esterified carboxy radical or a tetrazolyl radical, or, if $B_a$ represents a single bond, $Y_{2a}$ represents a cyano radical or a free, salified or esterified carboxy radical or a tetrazolyl radical, the said products of formula ($I_a$) being in all the possible racemic, enantiomeric and, diastereoisomeric isomer forms, as well as the addition salts with mineral and organic acids or with mineral and organic bases of the said products of formula ($I_a$).

The —$(CH_2)_{m1}$—$S(O)_{m2}$—X—$R_{10}$ radical as defined above can represent for example the radicals in which $(CH_2)_{m1}$ represents the values of an alkylene radical such as, for example, methylene, ethylene, n-propylene or n-butylene and $R_{10}$ can represent an alkyl or alkenyl radical chosen from the values defined above or an aryl radical also chosen from the values indicated above such as for example phenyl, biphenyl, naphthyl, tetrazolyl, the alkyl or alkenyl radical that can be represented by the $R_{10}$ radical can optionally be substituted by an aryl radical chosen from the values defined above, to form an aralkyl or aralkenyl radical.

These alkyl or alkenyl, aryl, aralkyl and arylalkenyl radicals can be substituted themselves as indicated above for these radicals.

The following radicals can be mentioned for example and in a non-exhaustive manner: —$SO_2$—$NH_2$, —$SO_2$—NH—$CH_3$, —$SO_2$—NH—$CF_3$, —$SO_2$—NH—$C_6H_5$, —$SO_2$—NH—$CH_2$—$C_6H_5$, —$CH_2$—$SO_2$—$NH_2$, —$CH_2$—$SO_2$—NH—$C_6H_5$, —$SO_2$—NH—CO—NH—$CH_3$, —$SO_2$—NH—CO—NH—$C_6H_5$, —$SO_2$—H—CO—NH—$CF_3$, —$SO_2$—NH—CO—NH—$CH_2$—$C_6H_5$, —$SO_2$—NH—CO—NH—D in which D represents a phenyl, pyridine or pyrimidine radical optionally substituted by a chlorine atom,

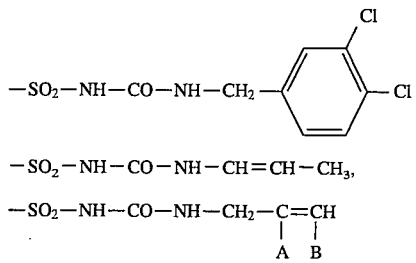

in which A and B, identical or different, are chosen from the hydrogen atom, the phenyl, pyridyl and pyrimidyl radicals,

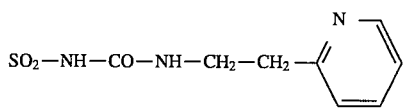

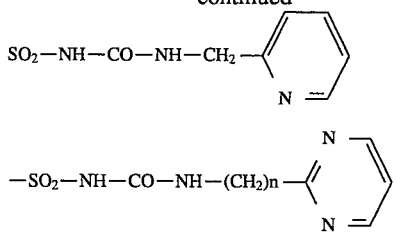

with n=1 or 2

The aryl radical that is represented by $Y_{1B}$ can be substituted by one or more radicals chosen from the values of $R_{2B}$ and $R_{3B}$ and in particular by the —NH—$(CH_2)_{m1}$—$SO_2$—X—$R_{10}$ and —CO—NH—$(CH_2)_{m1}$—$SO_2$—X—$R_{10}$ radicals in which the radical $(CH_2)_{m1}$—$SO_2$—X—$R_{10}$ can take for example the values indicated above.

There can be mentioned for example and in a nonexhaustive manner, the radicals: —NH—$SO_2$—$CH_3$, —NH—$SO_2$—$C_6H_5$, —NH—$SO_2$—$CF_3$, —NH—$CH_2$—$SO_2$—NH—$C_6H_5$, —CO—NH—$SO_2$—$C_2H_5$, —CO—NH—$SO_2$—$CH_3$, —CO—NH—$SO_2$—$CH_2$—$C_6H_5$.

A particular subject of the invention is the products of formula (I) as defined above in which:

$R_1$ represents an alkyl radical containing at most 4 carbon atoms, $R_2$ and $R_3$, identical or different, are chosen from the following radicals:

carboxy free, salified or esterified by a linear or branched alkyl radical containing at most 4 carbon atoms, formyl, acyloxy, alkyl containing at most 4 carbon atoms optionally substituted by a hydroxyl radical phenylthio, phenylsulphonyl, phenylsUlphinyl, alkylthio, alkylsulphonyl and alkylsulphinyl, in which the alkyl radical contains at most 4 carbon atoms, and Y represents the —Y1-B—$Y_2$ radical in which $Y_1$ represents a phenyl radical, B represents a single carbon-carbon bond and $Y_2$ represents a carboxy radical, free or esterified by a linear or branched alkyl radical containing at most 4 carbon atoms or a phenyl radical optionally substituted by a carboxy radical, free or esterified by a linear or branched alkyl radical containing at most 4 carbon atoms, the said products of formula (I) being in all the possible racemic, enantiomeric and diastereoisomeric isomer forms, as well as the addition salts with mineral and organic acids or with mineral and organic bases of the said products of formula (I).

A quite particular subject of the invention is the products of formula ($I_B$) corresponding to formula (I) as defined above, in which one of $R_2$ or $R_3$ represents an alkoxy, alkylthio or arylthio radical, these two latter radicals being optionally oxidized in the form of sulphoxide or sulphone and these three radicals being optionally substituted and the other represents a free, salified or esterified carboxy radical, the said products of formula (I) being in all the possible racemic, enantiomeric and diastereoisomeric isomer forms, as well as the addition salts with mineral and organic acids or with mineral and organic bases of the said products of formula (I).

Among the substituents of the alkylthio, alkoxy, arylthio and aryloxy radicals, optionally oxidized, there can be mentioned for example the following radicals: hydroxyl, alkoxy, free, salified or esterified carboxy, acyl, acyloxy, alkyl, phenyl, and halogen atoms.

Among the products which are a subject of the invention, there can be mentioned quite particularly the products of formula (I) corresponding to the following formulae:

2-butyl-1-[[2'-carboxy-(1,1'-biphenyl)-4-yl]-methyl]-4-(phenylthio)-1H-imidazole-5-carboxylic acid 2-butyl-1-[[2'-carboxy-(1,1'-biphenyl)-4-yl]-methyl]-4-(methylthio)-1H-imidazole-5-carboxylic acid 4'-[[2-butyl-4-(ethylthio)-5-(hydroxymethyl)-1H-imidazol-1-yl]-methyl]-(1,1'-biphenyl)-2-carboxylic acid 2-butyl-1-[[2'-carboxy-(1,1'-biphenyl)-4-yl]-methyl]-4-(ethylsulphonyl)-1H-imidazole-5-carboxylic acid 2-butyl-1-[[2'-carboxy-(1,1'-biphenyl)-4-yl]-methyl]-4-(ethylsulphinyl)-1H-imidazole-5-carboxylic acid 2-butyl-1-[[2'-carboxy-(1,1'-biphenyl)-4-yl]-methyl]-4-(ethylthio)-1H-imidazole-5-carboxylic acid 2-butyl-1-[[2'-carboxy-(1,1'-biphenyl)-4-yl]-methyl]-4-(phenylsulphonyl)-1H-imidazole-5-carboxylic acid 2-butyl-1-[[2'-carboxy-(1,1'-biphenyl)-4-yl]-methyl]-4-(phenylsulphinyl)-1H-imidazole-5-carboxylic acid 2-butyl-1-[[2'-tetrazolyl-(1,1'-biphenyl)-4-yl]-methyl]-4-(methylthio)-1H-imidazole-5-carboxylic acid.

Also a subject of the invention is a process for the preparation of products of formula ($I_B$) as defined above, characterized in that a compound of formula (II):

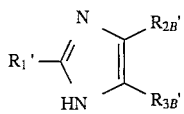

(II)

in which $R_1'$, $R_{2B}'$ and $R_{3B}'$ and have the meanings indicated above for $R_1$, $R_{2B}$ and $R_{3B}$ respectively and in which the optional reactive functions are optionally protected by protective groups, is reacted with a compound of formula (III):

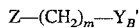

(III)

in which Z represents a halogen atom or a sulphonate and $Y_B'$ has the meaning indicated above for $Y_B$ in which the optional reactive functions are optionally protected by protective groups, in order to obtain a product of formula (IV):

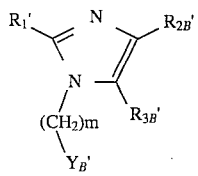

(IV)

in which $R_1'$, $R_{2B}'$, $R_{3B}'$ and $Y_B'$ have the meanings indicated above, which product of formula (IV) is subjected, if necessary and if desired, to one or more of the following reactions, in any order:

a) an elimination reaction of the protective groups that can be carried by the protected reactive functions, b) a salification reaction by a mineral or organic acid or by a base in order to obtain the corresponding salt, c) an esterification reaction of the acid function, d) a saponification reaction of the ester function into an acid function, e) a conversion reaction of the cyano function into an acid function, f) a reduction reaction of the carboxy function into an alcohol function, g) a conversion reaction of the alkoxy function into a hydroxyl function, h) an oxidation reaction of the alkylthio or arylthio group into a corresponding sulphoxide or sulphone, i) a conversion reaction of the sulphoxide or sulphone function into a corresponding sulphoximine function, j) an oxidation reaction of the alcohol function into an aldehyde or acid function, k) a conversion reaction of the nitrile function into tetrazole, l) a resolution reaction of the racemic forms into resolved products, m) a conversion reaction of the formyl radical into a carbamoyl radical, n) a conversion reaction of the carbamoyl radical into a nitrile radical, the said products of formula ($I_B$) thus obtained being in all the possible racemic, enantiomeric and diastereoisomeric lsomer forms.

In the preferred conditions for implementing the invention, the product of formula (IV) can be obtained by the addition of the product of formula (III) on to the free amine function of the imidazole of formula (II): in the product of formula (III), when Z represents a halogen atom, Z preferably represents a bromine atom but can also represent a chlorine or iodine atom; in the product of formula (III), Z can also represent a sulphonate of formula —O—SO$_2$— in which A preferably represents an alkyl radical containing at most 4 carbon atoms such as for example methyl or an aryl radical such as for example phenyl optionally substituted for example by an alkyl radical containing at most 4 carbon atoms such as for example methyl: A can thus represent, for example, the methyl radical or also the tolyl radical to give for example a tosylate.

The reaction of the product of formula (III) with the product of formula (II) can be achieved in a solvent such as for example dimethylformamide or also tetrahydrofuran, dimethoxyethane or dimethylsulphoxide under reflux of the solvent or at ambient temperature, preferably under agitation; the reaction is preferably carried out in the presence of a base such as for example sodium or potassium hydride or also sodium or potassium carbonate, sodium or potassium methylate or ethylate or tert-butylate.

According to the values of $R_1'$, $R_{2B}'$, $R_{3B}'$ and $Y_B'$, the products of formula (IV) constitute or do not constitute the products of formula ($I_B$).

The various reactive functions that can be carried by some of the compounds of the reactions defined above can, if necessary, be protected: they can be, for example, hydroxyl, acyl, free carboxy or also amino and monoalkylamino radicals which can be protected by the appropriate protective groups.

The following non-exhaustive list of examples of protection of reactive functions can be mentioned:

the hydroxyl groups can be protected for example by alkyl radicals such as tert-butyl, trimethylsilyl, tert-butyldimethylsilyl, methoxymethyl, tetrahydropyrannyl, benzyl or acetyl, the amino groups can be protected for example by acetyl, trityl, benzyl, tert-butoxycarbonyl, phthalimido radicals or other radicals known in the chemistry of the peptides, the acyl groups such as the formyl group can be protected for example in the form of cyclic or non-cyclic ketals such as dimethyl- or diethylketal or ethylene dioxyketal, the acid functions of the products described above can be, if desired, amidified by a primary or secondary amine for example in methylene chloride in the presence, for example, of 1-ethyl-3-(dimethylaminopropyl) carbodiimide hydrochloride at ambient temperature:

the acid functions can be protected for example in the form of esters formed with easily cleavable esters such as benzyl or terbutyl esters or esters known in the chemistry of the peptides.

The reactions to which the products of formula (IV) as defined above can be subjected, if desired or if necessary, can be carried out, for example, as indicated hereafter.

a) The elimination of the protective groups such as for example those indicated above can be carried out in the usual conditions known to a man skilled in the art, notably by an acid hydrolysis carried out with an acid such as hydrochloric acid, benzene sulphonic or paratoluene sulphonic acid, formic or trifluoroacetic acid or also by a catalytic hydrogenation.

The phthalimido group can be eliminated by hydrazine.

A list of the various protective group which can be used will be found for example in the Patent BF 2,499,995.

b) The products described above can, if desired, be subjected to salification reactions for example by a mineral or organic acid according to the usual methods known to a man skilled in the art.

c) The products described above can, if desired, be subjected, on the optional carboxy functions, to salification reactions by a mineral or organic base or to esterification reactions: these esterification and salification reactions can be carried out according to the usual methods known to a man skilled in the art.

d) The optional conversions of the ester functions into acid functions of the above-described products can be, if desired, carried out in the usual conditions known to a man skilled in the art, notably by alkaline or acid hydrolysis for example by soda or potash in an alcohol medium such as, for example, in methanol or also by hydrochloric or sulphuric acid.

e) The optional cyano functions of the products described above can be, if desired, converted into an acid function in the usual conditions known to a man skilled in the art, for example by a double hydrolysis carried out in an acid medium such as for example in a sulphuric acid, glacial acetic acid and water mixture, these three compounds preferably being in equal proportions, or also in a mixture of soda, ethanol and water under reflux.

f) The optional free or esterified carboxy functions of the above-described products can be, if desired, reduced to an alcohol function by methods known to a man skilled in the art: the optional esterified carboxy functions can be, if desired, reduced into an alcohol function by methods known to a man skilled in the art and notably by lithium-aluminium hydride in a solvent such as for example tetrahydrofuran or also dioxan or ethyl ether.

The optional free carboxy functions of the above-described products can be, if desired, reduced to alcohol functions notably by boron hydride.

g) The optional alkoxy functions, such as notably methoxy, of the above-described products can be, if desired, converted into a hydroxyl function in the usual conditions known to a man skilled in the art, for example by boron tribromide in a solvent such as for example methylene chloride, by pyridine hydrobromide or hydrochloride or also by hydrobromic or hydrochloric acid in water or acetic acid under reflux.

h) The optional alkylthio or arylthio groups of the products described above can, if desired, converted into corresponding sulphoxide or sulphone functions in the usual conditions known to a man skilled in the art, such as for example by peracids such as for example peracetic acid or metachloroperbenzoic acid or also by ozone, oxone, sodium periodate in a solvent such as for example methylene chloride or dioxane at ambient temperature.

The obtaining of the sulphoxide function can be promoted by an equimolar mixture of the product containing an alkylthio or arylthio group and the reagent such as notably a peracid.

The obtaining of the sulphone function can be promoted by a mixture of the product containing an alkylthio or arylthio group with an excess of the reagent such as notably a peracid.

i) The optional sulphide, sulphoxide or sulphone functions of the above-described products can be, if desired, converted into the corresponding sulphoxime functions in order to prepare the products in which $R_2$ or $R_3$ represents a radical:

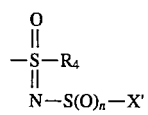

in the usual conditions known to a man skilled in the art: non-exhaustive examples of the preparation of products containing a sulphoximine function are described below.

Thus for example for the preparation of compounds such as N-(arylsulphonyl) sulphoximines and for example in the case where the aryl group that is represented by X' is a toluene radical, the sulphoximine can be obtained by the action of paratoluenesulphonic nitride on the corresponding sulphoxide, that being —S(O)CH$_3$, preferably in the presence of copper as indicated for example in the following reference: J. A. C. S., 95, pp. 4287 (1973) JOHNSON C.R. & coll.

Another method also used consists of treating N-tosylsulphilimine, itself prepared from the sulphide by the action, for example, of chloramine "T", with an oxidizing agent such as for example sodium hypochlorite in phase transfer conditions as indicated, for example, in the following reference: J. Org. Chem., 49, pp. 2282 (1984) AKUTAGAWA K. & coll.

j) The optional alcohol function of the products described above can be, if desired, converted into an aldehyde or acid function by oxidation in the usual conditions known to a man skilled in the art, such as for example by the action of manganese oxide to obtain the aldehydes or of Jones reagent to obhain the acids.

k) The optional nitrile functions of the products described above can be, if desired, converted into tetrazole in the usual conditions known to a man skilled in the art, such as for example by the cycloaddition of a metallic azide such as for example a trialkyltin azide on to the nitrile function as indicated in the method described in the article referenced as follows: J. Organometallic Chemistry, 33, 337 (1971) KOZIMA S. & coll.

l) The optional optically active forms of the products of formula ($I_B$) can be prepared by resolution of the racemics according to the usual methods known to a man skilled in the art.

The conversion reactions of the formyl radical into a carbamoyl radical and of the carbamoyl radical into a nitrile radical are carried out according to the usual conditions known to a man skilled in the art. These reactions as well as the conversion of the nitrile radical into tetrazole are carried out preferably when these substituents are carried in alpha position of the biphenyl substituent that can be represented by —$Y_B$.

The compounds of formula ($I_B$) as defined above as well as their addition salts with acids have useful pharmacological properties.

The products are endowed with antagonistic properties for the angiotensin II receptor and are thus notably inhibitors of the effects of angiotensin II, in particular of the vasoconstricting effect and also of the trophic effect at the level of the myocytes.

These properties justify their use in therapeutics and also a subject of the invention is, as medicaments, the products as defined by formula ($I_B$) above, the said products of formula ($I_B$) being in all the possible racemic or optically active isomer forms, as well as the addition salts with pharmaceutically acceptable mineral or organic acids of the said products of formula ($I_B$).

A particular subject of the invention is, as medicaments, the products of formulae (I), ($I_C$) and ($I_a$) as defined above and the products of formula ($I_B$) as defined above in which:

$R_1$ represents an alkyl radical containing at most 4 carbon atoms, $R_2$ and $R_3$, identical or different, are chosen from the following radicals:

carboxy free, salified or esterified by a linear or branched alkyl radical containing at most 4 carbon atoms, formyl, acyloxy, alkyl containing at most 4 carbon atoms optionally substituted by a hydroxyl radical, phenylthio, phenylsulphonyl, phenylsulphinyl, alkylthio, alkylsulphonyl and alkylsulphinyl, in which the alkyl radical contains at most 4 carbon atoms, and Y represents the —$Y_1$—B—$Y_2$ radical in which $Y_1$ represents a phenyl radical, B represents a single carbon-carbon bond and $Y_2$ represents a carboxy radical, free or esterified by a linear or branched alkyl radical containing at most 4 carbon atoms or a phenyl radical optionally substituted by a carboxy radical free or esterified by a linear or branched alkyl radical containing at most 4 carbon atoms, the said products of formula ($I_B$) being in all the possible racemic, enantiomeric and diastereoisomeric isomer forms, as well as the addition salts with mineral and organic acids or with mineral and organic bases of the said products of formula ($I_B$).

A quite particular subject of the invention is, as medicaments, the products of formula ($I_B$) corresponding to formula ($I_a$) as defined above, in which one of $R_{2a}$ or $R_{3a}$ represents an alkylthio or arylthio radical optionally oxidized in the form of sulphoxide or sulphone and optionally substituted as indicated above, and the other represents a free, salified or esterified carboxy radical, the said products of formula ($I_a$) being in all the possible racemic, enantiomeric and diastereoisomeric isomer forms, as well as the addition salts with pharmaceutically acceptable mineral and organic acids or mineral and organic bases of the said products of formula ($I_a$).

A more particular subject of the invention is, as medicaments, the products described hereafter in the examples and notably the following products of formula (I):

2-butyl-1-[[2'-carboxy-(1,1'-biphenyl)-4-yl]-methyl]-4-(phenylthio)-1H-imidazole-5-carboxylic acid 2-butyl-1-[[2'-carboxy-(1,1'-biphenyl)-4-yl]-methyl]-4-(methylthio)-1H-imidazole-5-carboxylic acid 4'-[[2-butyl-4-(ethylthio)-5-(hydroxymethyl)-1H-imidazol-1-yl]-methyl]-(1,1'-biphenyl)-2-carboxylic acid 2-butyl-1-[[2'-carboxy-(1,1'-biphenyl)-4-yl]-methyl]-4-sulphonyl)-1H-imidazole-5-carboxylic acid 2-butyl-1-[[2'-carboxy-(1,1'-biphenyl)-4-yl]-methyl]-4-ethylsulphonyl)-1H-imidazole-5-carboxylic acid 2-butyl-1-[[2'-carboxy-(1,1'-biphenyl)-4-yl]-methyl]-4-(ethylthio)-1H-imidazole-5-carboxylic acid 2-butyl-1-[[2'-carboxy-(1,1'-biphenyl)-4-yl]-methyl]-4-(phenylsulphonyl)-1H-imidazole-5-carboxylic acid 2-butyl-1-[[2'-carboxy-(1,1'-biphenyl)-4-yl]-methyl]-4-(phenylsulphinyl)-1H-imidazole-5-carboxylic acid 2-butyl-1-[[2'-tetrazolyl-(1,1'-biphenyl)-4-yl]-methyl]-4-(methylthio)-1H-imidazole-5-carboxylic acid as well as their addition salts with pharmaceutically acceptable mineral or organic acids.

The medicaments, which are a subject of the invention, can be used in the treatment of arterial hypertension, cardiac insufficiencies, renal insufficiencies and in the prevention of post-angioplasic reccurences of stenosis.

They can also be used in the treatment of certain gastro-intestinal and gynaecological disorders, and in particular for a relaxing effect at the level of the uterus.

The invention extends to pharmaceutical compositions containing as active ingredient at least one of the medicaments as defined above.

These pharmaceutical compositions can be administered by buccal or rectal route, by parenteral route or by local route as a topical application on the skin and the mucous membranes.

These compositions can be solid or liquid and can be presented in all the pharmaceutical forms currently used in human medicine such as, for example, plain or sugar-coated tablets, capsules, granules, suppositories, injectable preparations, ointments, creams, gels and aerosol preparations; they are prepared according to the usual methods. The active ingredient can be incorporated with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The usual dose, variable according to the product used, the patient treated and the affection in question, can be, for example, 1 to 100 mg per day for an adult, by oral route.

Some starting products of formula (II) are known and can be prepared for example as indicated in the European Patent EP 168,950.

The starting products of formula (II) can in particular be prepared according to a new process and the present invention thus also relates to this new preparation process for the starting products of formula (II) as defined above, characterized in that a compound of formula ($II_a$):

in which $R_{2B}'$ has the meaning indicated above for $R_{2B}$ in which the optional reactive functions are optionally protected by protective groups, is subjected to the action of a reducing agent, in order to obtain the corresponding amine of formula ($II_b$):

in which $R_{2B}'$ has the meaning indicated previously, which is subjected to the action of a compound of formula ($II_c$):

in which $R_1'$ has the meaning indicated above for $R_1$ in which the optional reactive functions are optionally protected by protective groups and W represents a hydroxyl radical or a halogen atom, in order to obtain a product of formula ($II_d$):

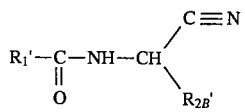 ($II_d$)

in which $R_1'$ and $R_{2B}'$ have the meanings indicated previously, which is reacted with a compound of formula ($II_e$):

$$R_{3B}'-SH \quad (II_e)$$

in which $R_{3B}'$ has the meaning indicated above for $R_{3B}$ in which the optional reactive functions are optionally protected by protective groups, in order to obtain a product of formula ($II_f$):

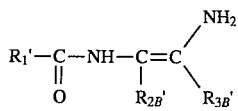 ($II_f$)

in which $R_1'$, $R_{2B}'$ and $R_{3B}'$ have the meanings indicated previously, which is subjected to a cyclization reaction in order to obtain a product of formula (II), which product of formula (II) is subjected, if desired and if necessary, to one or more of the following reactions, in any order:

a) an elimination reaction of the protective groups that can be carried by the protected reactive functions, b) a salification reaction by a mineral or organic acid or by a base in order to obtain the corresponding salt, c) an esterification reaction of the acid function, d) a saponification reaction of the ester function into an acid function, e) a conversion reaction of the cyano function into an acid function, f) a reduction reaction of the carboxy function into an alcohol function, g) a conversion reaction of the alkoxy function into a hydroxyl function, h) an oxidation reaction of the alkylthio or arylthio group into a corresponding sulphoxide or sulphone, i) a conversion reaction of the sulphoxide or sulphone function into a corresponding sulphoximine function, j) an oxidation reaction of the alcohol function into an aldehyde or acid function, k) a conversion reaction of the nitrile function into tetrazole, l) a resolution reaction of the racemic forms into resolved products, m) a conversion reactLion of the formyl radical into a carbamoyl radical, n) a conversion reaction of the carbamoyl radical into a nitrile radical, the said products of formula (II) thus obtained being in all the possible racemic, enantiomeric and diastereoisomeric isomer forms.

In the preferred conditions for implementing the invention, the above process is carried out in the following manner:

the reduction of the oxime of formula ($II_a$) to give the compound of formula ($II_b$) can be carried out according to the usual methods known to a man skilled in the art such as for example by an aluminium amalgam prepared in the usual conditions such as for example by the action of mercuric chloride on aluminium: the reaction is carried out in a solvent such as for example tetrahydrofuran or toluene, preferably at a temperature of approximately 50° C.;

the addition of the product of formula (IIc), in which W preferably represents a chlorine atom but can also represent a bromine atom, on to the amine of formula (IIb) thus obtained can be carried out according to methods known to a man skilled in the art such as for example in the presence of a base such as for example pyridine or also triethylamine; the reaction is preferably carried out at a temperature of approximately 0° C., the addition of the sulphurous derivative of formula ($II_e$) on to the amide of formula ($II_d$) thus obtained in order to obtain the product of formula ($II_f$) is carried out, for example, by solubilizing the amide of formula ($II_d$) in a solvent such as for example an alcohol such as ethanol or methanol, then successive additions of a base such as for example triethylamine and the compound of formula ($II_e$) preferably under agitation and at ambient temperature, the cyclization reaction of the compound of formula ($II_f$) thus obtained into a product of formula (II) can be carried out in a solvent such as, for example, dichloromethane, dichloroethane or also chloroform: the reaction can be carried out for example in the presence of phosphorous pentachloride ($PCl_5$) dissolved beforehand in dichoromethane at a temperature of approximately −78° C. in the presence of a base such as for example pyridine or dimethylaminopyridine: the reaction can be carried out under agitation at ambient temperature.

The product of formula (II) thus obtained can be subjected to one or more of the above-indicated reactions, these reactions being able to be carried out in the same conditions as those defined above for the products of formula (IV).

The compound of formula ($II_a$) can be, for example, ethylisonitrosocyanoacetate which can be found, for example, in the form of product commercially-available from LANCASTER under the reference 8930.

The starting compounds of formula (III) may be commercially available or can be prepared according to the usual methods known to a man of the art.

A preparation process for certain products of formula (III) as defined above, can consist of subjecting methyl iodobenzoate, for example, in the form of a product commercially available from JANSSEN, to the action of iodotoluene, for example, in the form of a product commercially available from FLUKA, the reaction being carried out for example in the presence of powdered copper at a temperature of approximately 100° C. to 300° C., in order to obtain a product:

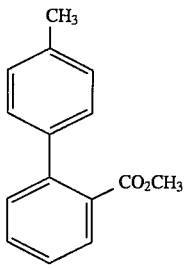

the esterified carboxy radical of which can, if desired, be released from the alkyl radical by standard methods known to a man skilled in the art or indicated above, for example acid or alkaline hydrolysis, which can be subjected to a bromination reaction on the methyl radical by standard methods known to a man skilled in the art, for example by the action of n-bromosuccinimide in carbon tetrachloride.

Examples of the preparation of compounds of formula (III) are described in the literature and examples are given notably in the U.S. Pat. No. 4,880,804 or for example in the reference Chemistry and Industry 7 September 1987 HOWARD and COLQUHOUN pp. 612–617.

Finally a subject of the present invention is as new industrial products and notably as intermediate products necessary for the preparation of the products of formula (I), the compounds of formula (II) in which $R_1'$ does not represent the methyl radical.

The following examples illustrate the invention without however limiting it.

PREPARATION 1

Ethyl 2-butyl-4-(ethylthio)-1H-imidazole-5-carboxylate

STAGE A

Ethyl aminocyano acetate.

4 g of aluminium in 40 cm$^3$ of a solution of 5% mercuric chloride in water is agitated for 2 minutes, then decanted, washed with water (twice with 30 cm$^3$) then with tetrahydrofuran. 150 cm$^3$ of tetrahydrofuran is added then a solution of 10 g of cyano-(hydroximino)-ethyl acetate in 60 cm$^3$ of tetrahydro-furan is introduced over 3 minutes. The temperature is maintained below 60° C. but above 47° C. After 15 minutes of agitation the reaction medium is filtered, and the insoluble part is washed with tetrahydrofuran. The filtrate is evaporated off under reduced pressure and 7 g of the desired product is obtained, used as it is for the following stage.

STAGE B

Ethyl cyano-[(1-oxo-pentyl)-amino]-acetate 4.24 cm$^3$ of pyridine, then over 30 minutes, 6.31 cm$^3$ of pentanoyl chloride are added to a solution agitated at 0° C. of 6.71 g of the product obtained in Stage A above in 100 cm$^3$ of methylene chloride, keeping the temperature below 6° C. The mixture is then evaporated to dryness under reduced pressure, the excess pyridine is entrained with toluene and the residue is taken up in 200 cm$^3$ of methylene chloride, washed twice with water then evaporated again under vacuum. After impasting the residue obtained in isopropyl ether, 8.4 g of the desired product is collected. M.p.=88° C.

STAGE C

Ethyl 3-amino-3-(ethylthio)-2-[(1-oxo-pentyl)-amino]-propenoate.

0.76 cm$^3$ of triethylamine and 8 cm$^3$ of ethanediol are added to a solution of 11.6 g of product obtained as in Stage B in 250 cm$^3$ of ethanol. The mixture is agitated at ambient temperature for 4 to 5 days, whilst carrying out daily additions of 8 cm$^3$ of ethancthiol until there is no more starting product. After evaporation to dryness under reduced pressure, the residue is impasted in ether and 10.8 g of desired product is obtained, M.p.=110° C. A second lot of 1.2 g of expected product is collected from the impasting mother liquors.

STAGE D

Ethyl 2-butyl-4-(ethylthio)-1H-imidazole-5-carboxylate.

1.96 g of dimethyl amino pyridine in solution in 10 cm$^3$ of methylene chloride, then a solution of 2 g of the product obtained in Stage C in 20 cm$^3$ of methylene chloride are added to a solution of 3.035 g of phosphorous pentachloride in 50 cm$^3$ of methylene chloride, cooled down to −78° C. The reaction medium is agitated for 16 hours at ambient temperature, then poured into 200 cm$^3$ of a solution of sodium bicarbonate, agitated for one hour and extracted with methylene chloride; the extracts are washed with water saturated with sodium chloride, dried, filtered and evaporated to dryness under reduced pressure. 2.6 g of residue is obtained which is chromatograhed on silica, (eluant: methylene chloride - acetone (9-1)). 1.24 g of the desired product is obtained.

| Analysis for $C_{12}H_{20}N_2O_2S$ = 256.355 | | | | |
| --- | --- | --- | --- | --- |
| | C | H | N | S |
| % calculated | 56.30 | 7.86 | 10.94 | 12.52 |
| % found | 56.20 | 7.90 | 10.70 | 12.40 |

| NMR Spectrum: 250 MHz ppm CDCl$_3$ | |
| --- | --- |
| $CH_3-CH_2$ | 0.93 (t) |
| $CO_2-CH_2-CH_3$ | 1.37 (t) |
| $S-CH_2-CH_3$ | 1.39 (t) |
| $-\underset{\underset{O}{\|\|}}{C}-CH_2-\underline{CH_2}-\underline{CH_2}-CH_3$ | approx. 1.37 (m)–1.71 (m) O |
| $-\underset{\underset{O}{\|\|}}{C}-CH_2-\underline{CH_2}$ | 2.73 (m) |
| $S-\underline{CH_2}-CH_3$ | 3.19 (q) |
| $CO_2-\underline{CH_2}-CH_3$ | 4.35 (q) |
| mobile proton | 10.0 |

PREPARATION 2

Ethyl 2-butyl-4-(phenylthio)-1H-imidazole-5-carboxylate

STAGE A

Ethyl 3-amino-2-[(1-oxo-pentyl)-amino]-3-(phenylthio)-propenoate.

The operation is carried out as in Stage C of Preparation 1 starting with 3 g of product obtained in Stage B of Preparation 1, using 2.9 cm$^3$ of thiophenol, then after 16 hours, another 1.45 cm$^3$ of thiophenol is added, agitation is carried out for another 48 hours and 3.92 g of the desired product is obtained, isolated after impasting in isopropyl ether. M.p.=115° C.

| Analysis for $C_{16}H_{22}N_2O_3S = 322.34$ | | | | |
|---|---|---|---|---|
| | C | H | N | S |
| % calculated | 59.60 | 6.88 | 8.69 | 9.94 |
| % found | 59.50 | 7.00 | 8.60 | 9.80 |

STAGE B

Ethyl 2-butyl-4-(phenylthio)-1H-imidazole-5-carboxylate

The operation is carried out as in Stage D of preparation 1 starting with 322 mg of the product obtained in Stage A above. After chromatography on silica (eluant: methylene chloride - acetone (9-1)), 210 mg of the desired product is obtained. M.p.=74° C.

| Analysis for $C_{16}H_{20}N_2O_2S = 304.41$ | | | | |
|---|---|---|---|---|
| | C | H | N | S |
| % calculated | 63.13 | 6.62 | 9.20 | 10.53 |
| % found | 62.70 | 6.60 | 9.10 | 10.30 |

PREPARATION 3

4-(ethylthio)-2-methyl-1H-imidazole-5-methanol 11.64 cm³ of a 1.2M solution of diisobutylaluminium hydride in toluene is added over 10 minutes at −70° C. to a solution of 1 g of ethyl 4-(ethylthio)-2-methyl-1H-imidazole-5-carboxylate (obtained as in Preparation 1 using, in Stage B, acetyl chloride instead of pentanoyl chloride) in 100 cm³ of methylene chloride. The mixture is agitated for 3 hours at ambient temperature then hydrolyzed by the addition of 1 cm³ of water. After agitation for 15 minutes, then filtering, the insoluble part is washed with 20 cm³ of methylene chloride then 5 times with 20 cm³ of a methylene chloride - methanol mixture (9-1). After drying, the filtrate is brought to dryness under reduced pressure. The residue (760 mg) is impasted in 7.6 cm³ of methylene chloride and 614 mg of the expected product is obtained. M.p.=153° C.

IR Spectrum:

Absence $\diagdown C=O \diagup$

| Absorption OH/NH complex region | |
|---|---|
| Heteroaromatic | 1582 cm⁻¹–1524 cm⁻¹ |

PREPARATION 4

2-butyl-4-(ethylthio)-1H-imidazole-5-methanol

The operation is carried out as in Preparation 3 starting with 500 mg of the product obtained in Preparation 1, and in this way 320 mg of the desired product is obtained. M.p.=128/130° C.

NMR Spectrum: DMSO CH₃—(CH₂)₃ 0.91 (t) CH₃— (CH₂)₂—CH₂ 1.37 (m)–1.68 (m) S—CH₂—CH₃ 1.18 (t) S—CH₂—CH₃ 3.09 (m) =C—CH₂—OH 4.64 (s) OH 4.56

EXAMPLE 1

Methyl 4'-[[5-(ethylthio)-4-(hydroxymethyl)-2-methyl-1H-imidazol-1-yl]-methyl]-(1,1'-biphenyl)-2-carboxylate 300 mg of product obtained in Preparation 3 in solution in 3 cm³ of dimethylformamide is added to a suspension of 95 mg of sodium methylate with 5 cm³ of dimethylformamide. The mixture is agitated for 20 minutes at ambient temperature then 1.19 g of methyl 4'-(bromomethyl)-(1,1'-biphenyl)-2-carboxylate in solution in 5 cm³ of dimethylformamide is added, agitation is carried out for one hour at ambient temperature, the mixture is poured into 100 cm³ of water, extracted with ethyl acetate, the extracts are washed with water saturated with sodium chloride, dried and evaporated to dryness under reduced pressure. The residue (1.5 g) is chromatographed on silica (eluant: methylene chloride - ethyl acetate - methanol (5-4-1)). 390 mg of the desired product, M.p.=150° C., and 165 mg of product of Example 3 are obtained.

| Analysis for $C_{16}H_{20}N_2O_2S = 304.41$ | | | | |
|---|---|---|---|---|
| | C | H | N | S |
| % calculated | 63.13 | 6.62 | 9.20 | 10.53 |
| % found | 62.70 | 6.60 | 9.10 | 10.30 |

| NMR Spectrum: CDCl₃ 250 MHz | |
|---|---|
| S—CH₂—CH₃ | 1.14 (t) |
| S—CH₂—CH₃ | 2.42 (q) |
| CH₂—OH | 4.74 (s) |
| 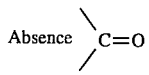 | 2.37 (s) |
| N—CH₂—C₆H₄ | 5.28 (s) |
| CO₂—CH₃ | 3.63 (s) |
| aromatics | 7.03–7.84 |

EXAMPLE 2

4'-[[5-(ethylthio)-4-(hydroxymethyl)-2-methyl-1H-imidazol-1-yl]-methyl]-(1,1'-biphenyl)-2-carboxylic acid A solution of 300 mg of the product obtained in Example 1 with 15 cm³ of ethanol and 0.75 cm³ of 2N sodium hydroxide solution is agitated for 7 hours under reflux. The mixture is cooled down, then neutralized by the addition of 0.75 cm³ of 2N hydrochloric acid, followed by evaporation to dryness under reduced pressure. Agitation is carried out for 15 minutes with 2 cm³ of water, followed by separation, and 255 mg of product is obtained 100 mg of which is recrystallized from 10 cm³ of isopropanol containing 0.5 cm³ water. 80 mg of the desired product is obtained. M.p.=205° C.

| Analysis for $C_{21}H_{22}N_2O_3S = 382.49$ | | | | |
|---|---|---|---|---|
| | C | H | N | S |
| % calculated | 65.94 | 5.79 | 7.32 | 8.38 |
| % found | 66.10 | 5.80 | 7.20 | 8.20 |

| NMR Spectrum: DMSO 250 MHz | |
|---|---|
|  | 2.28 (s) |
| $\underline{CH_2}$—OH | 4.40 (s) |
| $CH_2$—$\underline{OH}$ | 4.77 (s) |
| N—$\underline{CH_2}$—$C_6H_4$ | 5.30 (s) |
| S—$CH_2$—$\underline{CH_3}$ | 1.05 (t) |
| S—$\underline{CH_2}$—$CH_3$ | 2.41 (q) |
| $CO_2H$ | 12.70 |
| aromatics | 7.04 to 7.72 |

EXAMPLE 3

Methyl 4'-[[4-(ethylthio)-5-(hydroxymethyl)-2-methyl-1H-imidazol-1-yl]-methyl]-(1,1'-biphenyl)-2-carboxylate The desired product is obtained by chromatography as in Example 1. 165 mg of product is obtained.

| NMR Spectrum: $CDCl_3$ 250 MHz | |
|---|---|
|  | 2.35 (s) |
| S—$CH_2$—$\underline{CH_3}$ | 1.22 (t) |
| S—$\underline{CH_2}$—$CH_3$ | 2.81 (q) |
| $\underline{CH_2}$—$C_6H_4$ | 5.26 (s) |
| $\underline{CH_2}$—OH | 4.64 (s) |
| $CO_2CH_3$ | 3.64 (s) |
| aromatics | 7.02 to 7.84 |

EXAMPLE 4

4'-[[4-(ethylthio)-5-(hydroxymethyl)-2-methyl-1H-imidazol-1-yl]-methyl]-(1,1'-biphenyl)-2-carboxylic acid The operation is carried out as in Example 2 starting with 170 mg of the product obtained as in Example 3. 70 mg of the desired product is obtained, isolated after impasting in ethyl acetate. M.p.=250° C.

| Analysis for $C_{21}H_{22}N_2O_3S = 382.49$ | | | | |
|---|---|---|---|---|
| | C | H | N | S |
| % calculated | 65.94 | 5.79 | 7.32 | 8.38 |
| % found | 62.40 | 5.40 | 6.70 | 7.80 |

| NMR Spectrum: DMSO 300 MHz | |
|---|---|
|  | 2.19 (s) |
| S—$\underline{CH_2}$—$CH_3$ | 2.70 (q) |
| S—$CH_2$—$\underline{CH_3}$ | 1.14 (t) |
| $\underline{CH_2}$—OH | 4.44 (s) |
| $\underline{CO_2}$—$CH_3$ | 5.15 (m) |
| —$\underline{CH_2}$—$C_6H_4$ | 5.28 (s) |
| aromatics | 7.09–7.70 |

EXAMPLE 5

Ethyl 2-butyl-4-(ethylthio)-1-[[2'-(methoxycarbonyl)-(1,1'-biphenyl)-4-yl]-methyl]-1H-imidazole-5-carboxylate 257 mg of the product obtained in Preparation 1 with 340 mg of methyl 4'-(bromomethyl)-(1,1'-biphenyl)-2-carboxylate, 180 mg of potassium carbonate and 20 cm³ of dimethylformamide are agitated for 24 hours under reflux. Extraction is carried out with 4 times 100 cm³ of ethyl acetate, the extracts are washed with a saturated solution of sodium chloride, dried and evaporated to dryness under reduced pressure. The residue (500 mg) is chromatographed on silica, (eluant: essence G - ethyl acetate (82)). 258 mg of the desired product is obtained.

NMR Spectrum: $CDCl_3$ ppm $\underline{CH_3}$—$CH_2$—$CH_2$ 0.89 (t) $CO_2$—$CH_2$—$CH_3$ 1.33 (t) S—$CH_2$—$\underline{CH_3}$ 1.41 (t) $CH_3$—$\underline{CH_2}$ 1.2 to 1.5 (m) 1.67 (m) =C—$\underline{CH_2}$—$CH_2$ 2.65 (t) S—$\underline{CH_2}$—$CH_3$ 3.21 (q) $CO_2$—$\underline{CH_2}$—$CH_3$ 4.27 (q) N—$\underline{CH_2}$—$C_6H_4$ 5.56 (s)

EXAMPLE 6

2-butyl-1-[[2'-carboxy-(1,1'-biphenyl)-4-yl]-methyl]-4-(ethylthio)-1H-imidazole-5-carboxylic acid The operation is carried out as in Example 2 starting with 250 mg of the product obtained in Example 5. 180 mg of product is obtained which is recrystallized from 10 cm³ of acetone. 88 mg of the desired product is collected. M.P.= 196° C.

| Analysis for $C_{24}H_{26}N_2O_4S = 438.55$ | | | | |
|---|---|---|---|---|
| | C | H | N | S |
| % calculated | 65.73 | 5.97 | 6.39 | 7.31 |
| % found | 65.50 | 6.0 | 6.20 | 7.30 |

NMR Spectrum: DMSO 250 MHz $\underline{CH_3}$—$CH_2$—$CH_2$ 0.82 (t) $CH_3$—$\underline{CH_2}$—$CH_2$—$CH_2$ 1.30–1.55 (m) $\underline{CH_2}$—C 2.62 S—$CH_2$—$\underline{CH_3}$ 1.30 (t) S—$\underline{CH_2}$—$CH_3$ 3.07 (q) N—$\underline{CH_2}$—$C_6H_4$ 5.59 (s) aromatic H's 7.04–7.71

EXAMPLE 7

Ethyl 2-butyl-1-[[2'-[(1,1-dimethyl-ethoxy)-carbonyl]-(1,1'-biphenyl)-4-yl]-methyl]-4-(ethylthio)-1H-imidazole-5-carboxylate The operation is carried out as in Example 5 starting with 200 mg of the product obtained in Preparation 1, using 405 mg of tertbutyl 4'-(bromomethyl)-(1,1'-biphenyl)-2-carboxylate. After chromatography on silica (eluant: essence G - methylene chloride - ethyl acetate (50-45-5)), 325 mg of the desired product is obtained.

| NMR Spectrum: CDCl₃ ppm | |
|---|---|
| $CH_3-CH_2-CH_2-CH_2$ | 0.91 (t) |
| $S-CH_2-\underline{CH}_3, CO_2-\underline{CH}_3$ | 1.3–1.43 |
| $CH_3-\underline{CH}_2-CH_2-CH_2$ | |
| $\underline{CH}_2-CH_2-C=$ | 1.7 (m) |
| $CH_2-\underline{CH}_2-C=$ | 2.65 (t) |
| $S-\underline{CH}_2-CH_3$ | 3.21 (q) |
| $\overset{O}{\underset{\|}{-C}}-O-\underline{CH}_2-CH_3$ | 4.26 (q) |
| $N-\underline{CH}_2-C_6H_4$ | 5.27 (s) |
| aromatics | 7.02–7.77 |

EXAMPLE 8

2-butyl-1-[[2'-carboxy-(1,1'-biphenyl)-4-yl]-methyl]-4-(ethythio)-1H-imidazole-5-carboxylic acid 325 mg of the product obtained in Example 7 with 3 cm³ of methylene chloride and 1.1 cm³ of trifluoroacetic acid are agitated for 2 hours. The mixture is evaporated to dryness, entrained with 3 times 5 cm³ of toluene, and 183 mg of crude product is obtained. M.p.=156° C.

After recrystallization obtained by dissolution in 2 cm³ of hot methylene chloride and the addition of 2 cm³ of isopropyl ether, 120 mg of the desired product is obtained. M.p.=156° C.

| Analysis for C₂₆H₃₀N₂O₄S = 466.6 | | | | |
|---|---|---|---|---|
| | C | H | N | S |
| % calculated | 66.93 | 6.48 | 6.0 | 6.87 |
| % found | 66.50 | 6.4 | 5.8 | 6.80 |

| NMR Spectrum: CDCl₃ | |
|---|---|
| $\underline{CH}_3-CH_2$ | 0.83 (t) |
| $CH_3-(\underline{CH}_2)_2-$ | approx. 1.30 masked, 1.57 (m) |
| $\rangle\!\!-\underline{CH}_2$ | 2.66 (t) |
| 2-$\underline{CH}_3-CH_2$ | 1.21 (t) |
| $CO_2Et$ and $S-Et$ | 1.31 (t) |
| $S-\underline{CH}_2$ | 3.10 (q) |
| $CO_2-\underline{CH}_2-CH_3$ | 4.17 (q) |
| $N-\underline{CH}_2-C_6H_4$ | 5.58 (s) |
| aromatics | 7.03–7.71 |

EXAMPLE 9

Ethyl 2-butyl-4-(ethylthio)-1-[[(4-methoxy-carbonyl)-phenyl]-methyl]-1H-imidazole-5-carboxylate 20.6 mg of 50% sodium hydride in oil dispersed in 4 cm³ of dimethylformamide and a solution of 100 mg of the product obtained in Preparation 1 in 1 cm³ of dimethylformamide are agitated for 30 minutes. Then 107.1 mg of methyl 4-(bromomethyl)-benzoate is added. The medium is agitated for 5 hours under reflux, poured into water, and extracted with ethyl acetate; the extracts are washed, dried and evaporated to dryness under reduced pressure. 177 mg of desired product is obtained.

| NMR Spectrum: CDCl₃ | |
|---|---|
| $\underline{CH}_3-(CH_2)_3-$ | 0.86 (t) |
| $COO-CH_2-\underline{CH}_3$ | 1.29 (m) |
| $CH_3-\underline{CH}_2-CH_2$ | |
| $CH_3-CH_2-\underline{CH}_2-CH_2$ | 1.63 (m) |
|  | 2.59 (t) |
| $S-\underline{CH}_2-CH_3$ | 3.21 (q) |
| $S-CH_2-\underline{CH}_3$ | 1.41 (t) |
| $COO-\underline{CH}_3$ | 3.90 (s) |
| $COO-\underline{CH}_2-CH_3$ | 4.24 (q) |
| | 5.56 (s) |
| | 7.04 (d) |
| | 7.97 (d) |

EXAMPLE 10

2-butyl-1-[(4-carboxy-phenyl)-methyl]-4-(ethylthio)-1H-imidazole-5-carboxylic acid The operation is carried out as in Example 2 starting with 117 mg of the product obtained in Example 9. 60 mg of crude product is obtained which is recrystallized from acetone, in this way 35 mg of desired product is collected. M.p.=168° C.

| Analysis for C₁₈H₂₂N₂O₄S = 362.45 | | | | |
|---|---|---|---|---|
| | C | H | N | S |
| % calculated | 59.65 | 6.12 | 7.73 | 8.84 |
| % found | 59.70 | 6.3 | 7.5 | 8.80 |

| NMR Spectrum: DMSO | |
|---|---|
| $\underline{CH}_3-(CH_2)_3$ | 0.79 (t) |
| $CH_3-(\underline{CH}_2)_2-$ | 1.25 (m) |
| | 1.51 (m) |
| 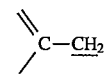 | 2.59 (t) |
| $S-CH_2-\underline{CH}_3$ | 1.3 (t) |
| $S-\underline{CH}_2-CH_3$ | 3.08 (q) |
| $N-CH_2-C_6H_4$ | 5.62 (s) |
| $H_3, H_5$ | 7.09 (d,l) |
| $H_2, H_6$ | 7.09 (d,l) |

EXAMPLE 11

Methyl 4'-[[2-butyl-4-(ethylthio)-5-(hydroxymethyl)-1H-imidazol-1-yl]-methyl]-(1,1'-biphenyl)-2-carboxylate The operation is carried out as in Example 1, starting with 2.35 g of the product obtained in Preparation 4, using 3.99 g of methyl 4'-(bromomethyl)-(1,1'-biphenyl)-2-carboxylate. 6.3 g of product is obtained which is chromatographed on silica (eluant: methylene chloride - acetone (5-5)). 609 mg of the desired product and 2.48 g of the product corresponding to Example 13 are obtained.

| NMR Spectrum: CDCl$_3$ 250 MHz | |
|---|---|
| C$\underline{H}_3$—(CH$_2$)$_3$ | 0.88 (t) |
| CH$_3$—(C$\underline{H}_2$)$_2$—CH$_2$ | 1.35 (m) |
|  | 1.69 (m) |
| 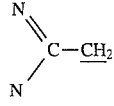 | 2.63 (m) |
| S—CH$_2$—CH$_3$ | 1.22 (t), 1.83 (q) |
| C$\underline{H}_2$—OH | 4.62 (s) |
| CO$_2$—C$\underline{H}_3$ | 3.63 (s) |
| C$\underline{H}_2$—C$_6$H$_4$ | 5.27 (s) |
| Aromatics | 7.01–7.84 |

EXAMPLE 12

4'-[[2-butyl-5-(ethylthio)-4-(hydroxymethyl)-1H-imidazol-1-yl]-methyl]-(1,1'-biphenyl)-2-carboxylic acid The operation is carried out as in Example 2 starting with 200 mg of the product obtained in Example 11. 176 mg is obtained which is recrystallized from 2.1 cm$^3$ of isopropanol containing 0.5 cm$^3$ water. 154 mg of desired product is collected. M.p.=208° C.

| Analysis for C$_{24}$H$_{28}$N$_2$O$_3$S = 424.54 | | | | |
|---|---|---|---|---|
|  | C | H | N | S |
| % calculated | 67.9 | 6.65 | 6.6 | 7.55 |
| % found | 67.9 | 6.5 | 6.5 | 7.50 |

NMR Spectrum: DMSO 250 MHz C$\underline{H}_3$—(CH$_2$)$_3$ 0.83 (t) CH$_3$—(C$\underline{H}_2$)$_2$—CH$_2$ 1.29 (m) 1.57 (m) S—CH$_2$—C$\underline{H}_3$ 1.03 (t) S—C$\underline{H}_2$ 2.42 (q) CH$_3$—(CH$_2$)$_2$—C$\underline{H}_2$ 2.58 (m) N—CH$_2$—C$_6$H 5.32 (s) —C$\underline{H}_2$—OH 4.41 (s, 1 ) mobile 1H 4.81 (m) Aromatics 7.01–7.71

EXAMPLE 13

Methyl 4'-[[2-butyl-5-(ethylthio)-4-(hydroxymethyl)-1H-imidazol-1-yl]-methyl]-(1,1'-biphenyl)-2-carboxylate The product is obtained during the chromatography of Example 11.

2.48 g of desired product is obtained. M.p.=110° C.

| NMR Spectrum: CDCl$_3$ 250 MHz | |
|---|---|
| C$\underline{H}_3$—(CH$_2$)$_3$ | 0.88 (m) |
| CH$_3$—(C$\underline{H}_2$)$_2$—C$\underline{H}_2$ | 1.35 (m) |
|  | 1.68 (m) |
| CH$_3$—(CH$_2$)$_2$—C$\underline{H}_2$ | 2.63 (m) |
| 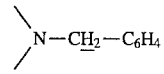 | 5.30 (s) |
| —C$\underline{H}_2$—OH | 4.76 (s) |
| S—CH$_2$—CH$_3$ | 1.12 (t) |
|  | 2.40 (q) |
| CO$_2$—C$\underline{H}_3$ | 3.63 (s) |
| Aromatics | 7.00 to 7.83 |

EXAMPLE 14

4'-[[2-butyl-4-(ethylthio)-5-(hydroxymethyl)-1H-imidazol-1-yl]-methyl]-(1,1'-biphenyl)-2-carboxylic acid The operation is carried out as in Example 2 starting with 163 mg of the product obtained in Example 13. 130 mg of product is obtained which is recrystallized from 1.5 cm$^3$ of isopropanol and 0.5 cm$^3$ of water. 26 mg of the desired product is collected. M.p.=160° C.

| Analysis for C$_{24}$H$_{28}$N$_2$O$_3$S = 424.57 | | | | |
|---|---|---|---|---|
|  | C | H | N | S |
| % calculated | 67.89 | 6.64 | 6.59 | 7.55 |
| % found | 66.8 | 6.7 | 6.5 | 7.80 |

NMR Spectrum: DMSO 250 MHz C$\underline{H}_3$—(CH$_2$)$_3$ 0.82 (t) CH$_3$—(C$\underline{H}_2$)$_2$—CH$_2$ 1.27 (m) 1.52 (m) CH$_3$—(CH$_2$)$_2$—C$\underline{H}_2$ 2.50 (masked) N—C$\underline{H}_2$—C$_6$H$_4$ 5.27 (s,1) S—CH$_2$—CH$_3$ 1.14 (t)–2.70 (q) —C$\underline{H}_2$—OH 4.44 (s,1) mobile 1 H 5.20 (m, wide) Aromatics 7.02–7.60

EXAMPLE 15

Ethyl 2-butyl-4-(ethylsulphinyl)-1-[[2'-(methoxycarbonyl)-(1,1'-biphenyl)-4-yl]-methyl]-1H-imidazole-5-carboxylate 500 mg of product obtained in Example 5 with 5 cm$^3$ of methylene chloride and 215 mg of meta chloroperbenzoic acid is agitated for 2 hours at ambient temperature. The mixture is poured into 50 cm$^3$ of water, extracted 3 times with 50 cm$^3$ of methylene chloride, the extracts are dried, filtered and brought to dryness under reduced pressure. The residue (675 mg) is chromatographed on silica (eluant: methylene chloride - acetone (6-4)). 400 mg of the desired product is obtained.

| IR Spectrum: CHCl$_3$ | |
|---|---|
| S=O | 1038 cm$^{-1}$ |
|  | 1716 cm$^{-1}$ |

| NMR Spectrum: CDCl$_3$ 250 MHz | |
|---|---|
| $-\overset{\overset{O}{\|}}{C}-O-CH_2-\underline{CH}_3$ <br> $-\overset{\overset{O}{\|}}{S}-CH_2-\underline{CH}_3$ | 1.32 (t) <br> 1.35 (t) |
| $\overset{\overset{O}{\|}}{S}-\underline{CH}_2-CH_3$ | 3.20 |
| $CO_2-\underline{CH}_3$ | 3.63 (d) |
| $CO_2Et$ | 4.32 (q) |
| $N-\underline{CH}_2-C_6H_4$ | 5.6 (AB) |
| $\underline{CH}_3-(CH_2)_2-CH_2$ | 0.89 (t) |
| $CH_2-(\underline{CH}_2)_2-CH_2$ | 1.4 (m) <br> 1.72 (m) |
| $CH_3-(CH_2)_2-\underline{CH}_2$ | 2.74 (m) |
| Aromatics | 7.02 to 7.84 |

EXAMPLE 16

2-butyl-1-[[2'-carboxy-(1,1'-biphenyl)-4-yl]methyl]-4-(ethylsulphinyl)-1H-imidazole-5-carboxylic acid The operation is carried out as in Example 2, starting with 0.2 g of the product obtained in Example 15. 154 mg of product is obtained which is recrystallized from an isopropanol - water mixture (3-7). 100 mg of the desired product is collected. M.p.=186° C.

| NMR Spectrum: DMSO 250 MHz | |
|---|---|
| $\underline{CH}_3-(CH_2)_2-CH_2$ | 0.82 (t) |
| $CH_3-(\underline{CH}_2)_2-CH_2$ | 1.29 <br> 1.57 |
| $CH_3-(CH_2)_2-\underline{CH}_2$ | 2.67 |
| $-\overset{\overset{O}{\|}}{S}-CH_2-CH_3$ | 1.12 (t) <br> 3.10 (q) |
| $\diagdown N-\underline{CH}_2-C_6H_4$ | 5.69 |
| Aromatics | 7.07–7.71 |

EXAMPLE 17

Ethyl 2-butyl-4-(ethylsulphonyl)-1-[[(2'-methoxycarbonyl)-(1,1'-biphenyl)-4-yl]-methyl)-1H-imidazole-5-carboxylate The operation is carried out as in Example 15 starting with 220 mg of the product obtained in Example 15, using 120 mg of metachloroperbenzoic acid. 400 mg of crude product is obtained which is chromatographed on silica (eluant: methylene chloride - ethyl acetate (7-3)) 209 mg of desired product is obtained.

| IR Spectrum: | |
|---|---|
| SO$_2$ | 1324 cm$^{-1}$ <br> 1136 cm$^{-1}$ |

| NMR Spectrum: CDCl$_3$ 250 MHz | |
|---|---|
| $\underline{CH}_3-(CH_2)_2-CH_2$ <br> $CH_3-(\underline{CH}_2)_2-CH_2$ | 0.83 (t) <br> 1.36 <br> 1.67 |
| $CH_3-(CH_2)_2-\underline{CH}_2$ | 2.70 |
| $SO_2-\underline{CH}_2-CH_3$ and <br> $-\overset{\overset{O}{\|}}{C}-O-CH_2-\underline{CH}_3$ | 1.36 and 1.42 |
| $SO_2-\underline{CH}_2-CH_3$ | 3.5 |
| $CO_2Et$ | 4.36 |
| $CO_2Me$ | 3.64 |
| Aromatics | 7.05 to 7.85 |

EXAMPLE 18

2-butyl-1-[[2'-carboxy-(1,1'-biphenyl)-4-yl]methyl]-4-(ethylsulphonyl)-1H-imidazole-5-carboxylic acid The operation is carried out as in Example 2 starting with 304 mg of the product obtained in Example 17. 210 mg of product is obtained which is recrystallized from a mixture of 2 cm$^3$ of isopropanol and 6 cm$^3$ of water. 111 mg of the desired product is collected. M.p.=192° C.

| Analysis for C$_{24}$H$_{26}$N$_2$O$_6$S = 470.26 | | | | |
|---|---|---|---|---|
| | C | H | N | S |
| % calculated | 61.29 | 5.52 | 5.95 | 6.80 |
| % found | 61.4 | 5.6 | 5.8 | 6.80 |

NMR Spectrum: DMSO 250 MHz $\underline{CH}_3-(CH_2)_2-CH_2$ 0.82 (t) $CH_3-\underline{CH}_2-(CH_2)_2$ 1.27 (m) $CH_3-CH_2-\underline{CH}_2-CH_2$ 1.54 (m) $CH_3-(CH_2)_2-\underline{CH}_2$ 2.66 (t) $S-CH_2 \underline{CH}_3$ 1.20 (t) $-\underline{CH}_2-C_6H_4$ 5.55 (s,1) Aromatics 7.10–7.72

EXAMPLE 19

Ethyl 2-butyl-1-[[2'-(methoxycarbonyl)-(1,1'-biphenyl)-4-yl]-methyl]-4-(phenylthio)-1H-imidazole-5

The operation is carried out as in Example 5, starting with 165 mg of the product obtained in Preparation 2. 410 mg product is obtained which is chromatographed on silica eluant: methylene chloride - ethyl acetate (95-5 ), and 163 mg of desired product and 102 mg of product of Example 23 are collected. $\underline{CH}_3-(CH_2)_2-CH_2$ 0.86 (t) $CH_3-\underline{CH}_2-(CH_2)_2$ 1.33 (m) $CH_3-CH_2-\underline{CH}_2-CH_2$ 1.62 (m) $CH_3-(CH_2)_2-\underline{CH}_2$ 2.63 (t) $CO_2Et$ 1.27 (t) 4.25 (q) $CO_2Me$ 3.62 (s) $N-\underline{CH}_2-C_6H_4$ 5.58 (s) Aromatics 7.03–7.82

EXAMPLE 20

2-butyl-1-[[2'-carboxy-(1,1'-biphenyl)-4-yl]methyl]-4-(phenylthio)-1H-imidazole-5-carboxylic acid The operation is carried out as in Example 2 starting with 122 mg of the product obtained in Example 19. 101 mg of product is obtained which is recrystallized from 2 cm$^3$ of isopropanol and 0.4 cm$^3$ of water. 86 mg of desired product is collected. M.p.=155° C.

Analysis for $C_{28}H_{26}N_2O_4S$ = 486.59

|  | C | H | N | S |
|---|---|---|---|---|
| % calculated | 69.12 | 5.39 | 5.76 | 6.59 |
| % found | 69.4 | 5.4 | 5.6 | 6.60 |

EXAMPLE 21

Ethyl
2-butyl-1-[[2'-(methoxycarbonyl)-(1,1'-biphenyl)-
4-yl]-methyl]-4-(methylthio)-1H-imidazole-
5-carboxylate The operation is carried out as in Example 5, starting with 0.6 g of ethyl 2-butyl-4-(methylthio)-1H-imidazole-5-carboxylate (prepared as indicated in Stages C and D of Preparation 1, replacing the ethanethiol with methanethiol), using 907 mg of methyl 4'-(bromomethyl)-(1,1'-biphenyl)-2-carboxylate. After chromatography on silica (eluant: methylene chloride - ethyl acetate (97-3)) 0.8 g of the desired product is obtained.

NMR Spectrum: CDCl₃ 250 MHz C̲H₃—(CH₂)₃— 0.83 (t) CH₃—C̲H₂—(CH₂)₂ 1.38 (m) CH₃—CH₂—C̲H₂—CH₂ 1.67 (m) CH₃—(CH₂)₂—C̲H₂ 2.67 (t) S—CH₃ 2.61 (s) CO₂Et 1.3 (t) 4.28 (q) CO₂Me 3.62 (s) N—C̲H₂—C₆H₄ 5.57 (s) Aromatics 7.03 to 7.82

EXAMPLE 22

2-butyl-1-[[2'-carboxy-(1,1'-biphenyl)-4-yl]-
methyl]-4-(methylthio)-1H-imidazole-5-carboxylic
acid The operation is carried out as in Example 2 starting with 505 mg of the product obtained in Example 21. 395 mg of product is obtained which is recrystallized from a mixture of 12 cm³ of isopropanol and 8 cm³ of water. 305 mg of the desired product is collected. M.p.=220° C.

Analysis for $C_{23}H_{24}N_2O_4S$ = 424.52

|  | C | H | N | S |
|---|---|---|---|---|
| % calculated | 65.11 | 5.70 | 6.60 | 7.55 |
| % found | 65.3 | 5.9 | 6.4 | 7.40 |

NMR Spectrum: DMSO 250 MHz C̲H₃—(CH₂)₃— 0.82 (t) CH₃—(C̲H₂)₂—CH₂ 1.23-1.54 (m) CH₃—(CH₂)₂—C̲H₂ 2.63 (t) S—C̲H₃ 2.46 (s) N—C̲H₂—C₆H₄ 5.6 (s) Aromatics 7.04 to 7.70 mobile 1H 12.74 (s)

EXAMPLE 23

Ethyl 2-butyl-1-[[2'-(methoxycarbonyl)-
(1,1'-biphenyl)-4-yl]-methyl]-5-(phenylthio)-
1H-imidazole-4-carboxylate The operation is carried out as in Example 19 and after chromatography 102 mg of the desired product is collected.

NMR Spectrum: CDCl₃ 250 MHz C̲H₃—(CH₂)₃— 0.87 (t) CH₃—C̲H₂—(CH₂)₂— 1.63 (m) CH₃—CH₂—C̲H₂—CH₂— 1.65 (m) CH₃—(CH₂)₂—C̲H₂ 2.68 (m) CO₂Et 1.33 (t) 4.39 (q) CO₂CH₃ 3.62 (s) N—C̲H₂—C₆H₄ 5.26 (s) Aromatics 7.05 to 7.84

EXAMPLE 24

2-butyl-1-[[2'-carboxy-(1,1'-biphenyl)-4-yl]-
methyl]-5-(phenylthio)-1H-imidazole-4-carboxylic
acid The operation is carried out as in Example 2, starting with 160 mg of the product obtained in Example 23. 146 mg of product is obtained which is recrystallized from a mixture of 3 cm³ of isopropanol and 0.6 cm³ of water. 113 mg of desired product is collected. M.p.=214° C.

Analysis for $C_{28}H_{26}N_2O_4S$ = 486.59

|  | C | H | N | S |
|---|---|---|---|---|
| % calculated | 69.12 | 5.39 | 5.76 | 6.59 |
| % found | 69.3 | 5.5 | 5.6 | 6.50 |

NMR Spectrum: DMSO 300 MHz C̲H₃—(CH₂)₃— 0.82 (t) CH₃—C̲H₂—(CH₂)₂— 1.28 (m) CH₃—(CH₂)—C̲H₂—CH₂— 1.55 (m) CH₃—(CH₂)₂—C̲H₂ 2.64 (m) N—C̲H₂—C₆H₄ 5.31 (s,1) Aromatics 6.96 to 7.71

EXAMPLE 25

Ethyl
2-butyl-1-[[2'-(methoxycarbonyl)-(1,1'-biphenyl)-
4-yl]-methyl]-4-(phenylsulphonyl)-1H-imidazole-
5-carboxylate The operation is carried out as in Example 17 starting with 264 mg of the product obtained in Example 19. After chromatography on silica (eluant: methylene chloride - ethyl acetate (95-5)), 176 mg of the desired product is obtained.

| IR Spectrum: CHCl₃ | |
|---|---|
| C=O | 1719 cm⁻¹ |
| Aromatics + heterocycles | } 1598, 1575, 1518, 1491, 1482 cm⁻¹ |
| SO₂ | 1327 cm⁻¹ |
|  | 1155 cm⁻¹ |

NMR Spectrum: CDCl₃ 300 MHz C̲H₃—(CH₂)₃— 0.86 (t) CH₃—C̲H₂—(CH₂)₃— 1.31 (m) CH₃—CH₂—C̲H₂—CH₂— 1.62 (m) CH₃—(CH₂)₂—CH₂ 2.66 (m) CO₂Et 1.31–4.33 (q) CO₂Me 3.61 (s) N—C̲H₂—C₆H₄ 5.42 (s) Aromatics 7.04 to 8.08

EXAMPLE 26

2-butyl-1-[[2'-carboxy-(1,1'-biphenyl)-4-yl]-methyl]-
4-(phenylsulphonyl)-1H-imidazole-5-carboxylic
acid The operation is carried out as in Example 2, starting with 150 mg of the product obtained in Example 25. After recrystallization from aqueous isopropanol, 110 mg of the desired product is obtained. M.p.=140° C.

Analysis for $C_{28}H_{26}N_2O_6S$ = 518.59

|  | C | H | N | S |
|---|---|---|---|---|
| % calculated | 64.85 | 5.05 | 5.40 | 6.18 |
| % found | 64.3 | 5.1 | 5.3 | 6.00 |

NMR Spectrum: DMSO 250 MHz C̲H₃—(CH₂)₃— 0.78 (t) CH₃—C̲H₂—(CH₂)₂— 1.23 (m) CH₃—CH₂—C̲H₂—CH₂— 1.46 (m) CH₃—(CH₂)₂—C̲H₂ 2.58 (m) N—C̲H₂—C₆H₄ 5.44 (s) Aromatics 7.10–7.95

EXAMPLE 27

Ethyl 2-butyl-1-[[2'-(methoxycarbonyl)-(1,1-biphenyl)-4-yl]-methyl]-4-(phenylsulphinyl)-1H-imidazole-5-carboxylate The operation is carried out as in Example 15, starting with 264 mg of the product obtained in Example 19, using 101 mg of metachloroperbenzoic acid. After chromatography on silica (eluant: methylene chloride - ethyl acetate (9-1)), 160 mg of desired product is obtained.

| IR Spectrum: CHCl₃ | |
|---|---|
| C═O | 1716 cm⁻¹ |
| Aromatics + heterocycles | } 1600, 1515, 1484 cm⁻¹ |
| S═O | 1036 cm⁻¹ |

NMR Spectrum: CDCl₃ 250 MHz C̲H₃—(CH₂)₃— 0.84 (t) CH₂—C̲H₂—(CH₂)₂— 1.27 (m) CH₃—CH₂—C̲H₂—CH₂— 1.60 (m) CH₃—(CH₂)₂—C̲H₂ 2.67 (m) CO₂Et 1.37 (t)–4.36 (q) CO₂Me 3.62 (s) Aromatics 6.98 to 7.83

EXAMPLE 28

2-butyl-1-[[2'-carboxy-(1,1'-biphenyl)-4-yl]-methyl]-4-(phenylsulphinyl)-1H-imidazole-5-carboxylic acid The operation is carried out as in Example 2, starting with 138 mg of the product obtained in Example 27. After recrystallization from aqueous isopropanol, 106 mg of the desired product is obtained. M.p.=195° C.

| Analysis for C₂₈H₂₆N₂O₅S = 502.59 | | | | |
|---|---|---|---|---|
| | C | H | N | S |
| % calculated | 66.91 | 5.21 | 5.57 | 6.37 |
| % found | 66.4 | 5.1 | 5.5 | 6.20 |

| IR Spectrum: General absorption NH/OH 3340 cm⁻¹ | |
|---|---|
| C═O | 1695 cm⁻¹ |
| Aromatics + heterocycles | } 1597, 1580, 1520, 1487 cm⁻¹ |
| S═O | 1025 cm⁻¹ |

NMR Spectrum: DMSO 250 MHz C̲H₃—(CH₂)₃— 0.75 (t) CH₂—CH₂—(C̲H₂)₂— 1.19 (m) CH₃—CH₂—C̲H₂—CH₂— 1.43 (m) CH₃—(CH₂)₂—C̲H₂ 2.59 (m) N—C̲H₂—C₆H₄ 5.65 (A, B system) Aromatics 7.05 to 7.70

EXAMPLE 29

Ethyl 2-butyl-1-[[2'-(methoxycarbonyl)-(1,1'-biphenyl)-4-yl]-methyl]-5-(phenylsulphonyl)-1H-imidazole-4-carboxylate The operation is carried out as in Example 25, starting with 264 mg of the product obtained in Example 23, using 242 mg of 85% metachloroperbenzoic acid. After chromatography on silica, (eluant: methylene chloride - ethyl acetate (9-1)), 216 mg of desired product is obtained.

NMR Spectrum: CDCl₃ 250 MHz C̲H₃—(CH₂)₃— 0.87 (t) CH₃—C̲H₂—(CH₂)₂— 1.34 (m) CH₃—CH₂—C̲H₂—CH₂— 66 (m) CH₃—(CH₂)₂—C̲H₂ 2.65 (m) N—C̲H₂—C₆H₄ 5.63 (s) CO₂CH₃ 3.66 (s) CO₂Et 1.42 (t) 4.46 (q) aromatic H's 6.88 to 7.87

| IR Spectrum: CHCl₃ | |
|---|---|
| C═O | 1728 cm⁻¹ |
| Aromatics + heterocycles | } 1597, 1585, 1565, 1518, 1499 cm⁻¹ |
| SO₂ | 1130 cm⁻¹ |
| | 1149 cm⁻¹ |

EXAMPLE 30

2-butyl-1-[[2'-carboxy-(1,1'-biphenyl)-4-yl]-methyl]-5-(phenylsulphonyl)-1H-imidazole-4-carboxylic acid The operation is carried out as in Example 2, starting with 190 mg of the product obtained in Example 29. 160 mg of a product is obtained which is recrystallized from aqueous methanol, and 135 mg of the desired product is collected. M.p.=155° C.

| Analysis for C₂₈H₂₆N₂O₆S = 518.59 | | | | |
|---|---|---|---|---|
| | C | H | N | S |
| % calculated | 64.85 | 5.05 | 5.40 | 6.18 |
| % found | 65.0 | 5.1 | 5.4 | 6.10 |

NMR Spectrum: DMSO 250 MHz C̲H₃—(CH₂)₃— 0.78 (t) CH₃—(C̲H₂)₂—CH₂ 1.24–1.51 (m) CH₃—(CH₂)₂—C̲H₂ 2.56 (m) N—C̲H₂—C₆H₄ 5.58 (s) Aromatics 6.82 to 7.89

In addition to the products described in the above exaples, which illustrate the invention without however limiting it, the products corresponding to formula (I) as defined above in which:

$R_1$ represents a butyl radical,

Y represents a biphenyl radical substituted in ortho position of the phenyl radical not linked to the CH₂ radical by a free or esterified carboxy radical or a tetrazolyl radical, and $R_2$ and $R_3$, identical or different, are chosen from the following radicals: mercapto, methylthio, propylthio, butylthio, allylthio, fluoromethylthio, trifluoromethylthio, 2,2,2-trifluoroethylthio, 3,3,3-trifluoropropylthio, vinylthio, 2-fluoroethylthio, phenylthio, benzylthio, 4-hydroxybenzylthio, 4-trifluoromethyl)-benzylthio, 2-pyridylthio, (2-pyridyl)methylthio, (4-methyl-1-piperazinyl)-methylthio, 2-(4-morpholinyl)-ethylthio, 2-[4-(3-methoxyphenyl)-1-piperazinyl]-ethylthio, 2-(benzyloxy)-ethylthio, 2-methoxy ethylthio, amino methylthio, 2-amino ethylthio (methylamino) methylthio, (diethylamino) methylthio, hydroxy methylthio, 2-hydroxy ethylthio, carboxy methylthio, (ethoxycarbonyl) methylthio, (tert-butoxycarbonyl) methylthio, 2-carboxy ethylthio, methylsulphinyl, ethylsulphinyl, propylsulphinyl, butylsulphinyl, phenylsulphinyl, methylsulphonyl, ethylsulphonyl, chlorosulphonyl, phenylsulphonyl, aminosulphonyl, fluoromethylsulphonyl, 2-(trimethylsilyl)-ethylsulphonyl, 2-fluoro-ethylsulphonyl, carboxy, ethoxycarbonyl, carboxymethyl, hydroxymethyl, formula, acetoxymethyl, N-tosyl methyl-sulphonimidoyl or N-tosyl phenylsulphonimidoyl, constitute products which can be obtained within the scope of the present invention.

EXAMPLE 31

Methyl 4'-[[2-butyl-5-(ethylsulphinyl)-4-(hydroxymethyl)-1H-imidazol-1-yl]-methyl]-(1,1'-biphenyl)-2-carboxylate The operation is carried out as in Example 15 starting with 500 mg of product obtained as in Example 13 in 7.5 cm³ of methylene chloride and 239 mg of metachloroperbenzoic acid. 287 mg of expected product is obtained.

| NMR Spectrum: CDCl₃ | |
|---|---|
| C$\underline{H_2}$—OH | 4.78 (s) |
| —S(=O)—C$\underline{H_2}$—CH₃ | 2.51 (m) and 3.12 (m) |
| —S(=O)—CH₂—C$\underline{H_3}$ | 1.13 |
| CH₂—(CH₂)₂—C$\underline{H_3}$ | 0.93 (t) |
| CH₂—(C$\underline{H_2}$)₂—CH₃ | 1.40 (m) 1.74 (m) |
| C$\underline{H_2}$—(CH₂)₂—CH₃ | 2.70 (t) |
| N—C$\underline{H_2}$—C₆H₄ | 5.23 (d, J=16.5) 5.46 (d, J=16.5) |
| CO₂—C$\underline{H_3}$ | 3.67 (s) |
| aromatics | 7.05 to 7.87 |

EXAMPLE 32

4'-[[2-butyl-5-(ethylsulphinyl)-4-(hydroxymethyl)-1H-imidazol-1-yl]-methyl]-(1,1'-biphenyl)-2-carboxylic acid The operation is carried out as in Example 2 starting with 287 mg of the product obtained in Example 31. 170 mg of expected product is obtained. M.p.=240° C.

| Analysis for C₂₄H₂₈N₂O₄S = 440.27 | | | | |
|---|---|---|---|---|
| | C | H | N | S |
| % calculated | 65.40 | 6.40 | 6.36 | 7.26 |
| % found | 65.5 | 6.4 | 6.5 | 7.40 |

| NMR Spectrum: DMSO 250 MHz | |
|---|---|
| C$\underline{H_2}$—OH | 4.49 |
| —S(=O)—C$\underline{H_2}$—CH₃ | 2.75 (m) and 3.06 (m) |
| —S(=O)—CH₂—C$\underline{H_3}$ | 1.01 (t) |
| N—C$\underline{H_2}$—C₆H₄ | 5.54 (m) |
| CH₂—(CH₂)₂—C$\underline{H_3}$ | 0.84 (t) |
| CH₂—(C$\underline{H_2}$)₂—CH₃ | 1.3 (m) 1.57 (m) |
| C$\underline{H_2}$—(CH₂)₂—CH₃ | 2.65 (t) |
| aromatics | 7.12 to 7.74 |

EXAMPLE 33

Methyl 4'-[[2-butyl-5-(ethylsulphonyl)-4-hydroxymethyl)-1H-imidazol-1-yl]-methyl]-(1,1'-biphenyl)-2-carboxylate The operation is carried out as in Example 15 starting with 500 mg of product obtained in Example 13 in 5 cm³ of methylene chloride and 474 mg of metachloroperbenzoic acid. 328 mg of expected product is obtained.

| NMR Spectrum: CDCl₃ | |
|---|---|
| C$\underline{H_2}$—OH | 4.79 (s) |
| —S(=O)₂—C$\underline{H_2}$—CH₃ | 2.79 (q) |
| —S(=O)₂—CH₂—C$\underline{H_3}$ | 1.13 (t) |
| CH₂—(CH₂)₂—C$\underline{H_3}$ | 0.94 (t) |
| CH₂—(C$\underline{H_2}$)₂—CH₃ | 1.42 (m) 1.78 (m) |
| C$\underline{H_2}$—(CH₂)₂—CH₃ | 2.75 (t) |
| N—C$\underline{H_2}$—C₆H₄ | 5.49 (s) |
| CO₂—C$\underline{H_3}$ | 3.67 (s) |
| aromatics | 7.04 to 7.85 |

EXAMPLE 34

4'-[[2-butyl-5-(ethylsulphonyl)-4-(hydroxymethyl)-1H-imidazol-1-yl]-methyl]-(1,1'-biphenyl)-2-carboxylic acid The operation is carried out as in Example 2 starting with 300 mtg of the,product obtained in Example 33. 160 mg of expected product is obtained. M.p.=210° C.

| Analysis for C₂₄H₂₈N₂O₅S = 456.27 | | | | |
|---|---|---|---|---|
| | C | H | N | S |
| % calculated | 63.17 | 6.18 | 6.13 | 7.02 |
| % found | 63.5 | 6.2 | 6.2 | 7.0 |

| NMR Spectrum: DMSO 250 MHz | |
|---|---|
| C$\underline{H_2}$—OH | 4,61 (s) |
| —S(=O)₂—C$\underline{H_2}$—CH₃ | 2.89 (q) |
| —S(=O)₂—CH₂—C$\underline{H_3}$ | 1.04 (t) |
| N—C$\underline{H_2}$—C₆H₄ | 5.53 (s) |
| CH₂—(CH₂)₂—C$\underline{H_3}$ | 0.85 (t) |
| CH₂—(C$\underline{H_2}$)₂—CH₃ | 1.31 (m)–1.60 (m) |

-continued

| NMR Spectrum: DMSO 250 MHz | |
|---|---|
| $\underline{CH_2}-(CH_2)_2-CH_3$ | 2.74 (t) |
| $CO_2-CH_3$ | 3.67 (s) |
| aromatics | 7.09 to 7.74 |

EXAMPLE 35

Ethyl 2-butyl-4-(methylsulphonyl)-1-[[2'-(methoxycarbonyl)-(1,1'-biphenyl)-4-yl]-methyl]-1H-imidazole-5-carboxylate The operation is carried out as in Example 15 starting with 244 mg of the product obtained in Example 21 using 222 mg of metachloroperbenzoic acid. 480 mg of crude product is obtained which is chromatographed on silica (eluant: methylene chloride - ethyl acetate (7-3)). 300 mg of desired product is obtained.

| IR Spectrum: | |
|---|---|
| $SO_2$ | 1318 cm$^{-1}$–1157 cm$^{-1}$ |
| NMR Spectrum: CDCl$_3$ 250 MHz | |
| $\underline{CH_3}-(CH_2)_2-CH_2$ | 0.90 (t) |
| $CH_3-(\underline{CH_2})_2-CH_2$ | 1.37 (m)–1.68 (m) |
| $CH_3-(CH_2)_2-\underline{CH_2}$ | 2.70 (m) |
| $\begin{array}{c}O\\\parallel\\-C-O-CH_2-CH_3\end{array}$ | 1.37 (t) and 4.37 (q) |
| $SO_2-\underline{CH_3}-$ | 3.34 (s) |
| $N-\underline{CH_2}-C_6H_4$ | 5.54 (s) |
| $CO_2ME$ | 3.64 (m) |
| Aromatics | 7.06 to 7.85 |

EXAMPLE 36

2-butyl-1-[[2'-carboxy-(1,1'-biphenyl)-4-yl]-methyl]-4-(methylsulphonyl)-1H-imidazole-5-carboxylic acid The operation is carried out as in Example 2 starting with 217 mg of the product obtained in Example 35. 210 mg of product is obtained which is recrystallized from a mixture of isopropanol and water (80-20). 150 mg of desired product is collected. M.p.=196° C.

| Analysis for $C_{24}H_{26}N_2O_6S = 470.26$ | | | | |
|---|---|---|---|---|
| | C | H | N | S |
| % calculated | 60.5 | 5.25 | 6.13 | 7.00 |
| % found | 60.8 | 5.3 | 6.1 | 6.90 |

| NMR Spectrum: DMSO 250 MHz | |
|---|---|
| $\underline{CH_3}-(CH_2)_2-CH_2$ | 0.83 (t) |
| $CH_3-(\underline{CH_2})_2-CH_2$ | 1.29 (m) |
| | 1.55 (m) |
| $CH_3-(CH_2)_2-\underline{CH_2}$ | 2.66 (t) |
| $\begin{array}{c}\phantom{O}\diagup S\diagdown CH_3\\O\phantom{//}\diagdown\phantom{/} O\end{array}$ | 1.20 (t) |

| NMR Spectrum: DMSO 250 MHz | |
|---|---|
| $N-\underline{CH_2}-C_6H_4$ | 5.58 (s) |
| Aromatics | 7.10–7.72 |

EXAMPLE 37

Ethyl 4-[2-(acetyloxy)-ethylthio]-2-butyl-1-[[2'-(methoxycarbonyl)-(1,1'-biphenyl)-4-yl]-methyl]-1H-imidazole-5-carboxylate The operation is carried out as in Example 5 starting with 6.49 g of ethyl 4-[2-(acetyloxy)-ethylthio]-2-butyl-1H-imidazole-5-carboxylate obtained as indicated in the preparation below and 7.56 g of a bromine derivative. 10.31 g of expected product is obtained after chromatographing on silica (eluant: methylene chloride - acetone (98-2 )) .

NMR Spectrum: $\underline{CH_3}-(CH_2)_2-CH_2$ 0.89 (t) $CH_3-(\underline{CH_2})_2-CH_2$ 1.33 (m) 1.67 (m) $CH_3-(CH_2)_2-\underline{CH_2}$ 2.63 (m) $CO-CH_3$ (imidazole) 2.08 (s) $CO_2-CH_2-\underline{CH_3}$ 1.33 (t) $CO_2-\underline{CH_2}-CH_3$ 4.27 (q) $S-\underline{CH_2}-CH_2-O-CO-$ 3.44 (t) $S-CH_2-\underline{CH_2}-O-CO$ 4.39 (t) $CO_2-\underline{CH_3}$ (phenyl) 3.62 (s) $N-\underline{CH_2}-C_6H_4$ 5.55 (s) Aromatics 7.02 to 7.81

Preparation of Ethyl 4-[2-(acetyloxy)-ethylthio]-2-butyl-1H-imidazole-5-carboxylate used at the start of Example 37

STAGE A 2-(acetyloxy)-ethylthio

Acetic anhydride is added slowly, at a temperature lower than 40° C., to a mixture containing 55 g of mercaptoethanol and 2.2 cm$^3$ of a 10% solution of sulphuric acid in acetic acid. The mixture is heated to 60° C. for 1 hour then left for 20 hours at ambient temperature. 500 cm$^3$ of ether is added, followed by washing with water, drying, and evaporating the solvents. After distilling the residue at 62°–64° C. (16 mm Hg) 75.78 g of expected product is obtained.

STAGE B

Ethyl 3-amino-3-(2-acetyloxy-ethylthio)-2-[(1-oxopentyl)-amino]propenoate 14 g of product obtained in stage B of preparation 1 is dissolved in 300 cm$^3$ of ethanol, 668 mg of triethylamine is added drop by drop then 9.52 g of product obtained in stage A above is added. The whole is left for 5 days at ambient temperature, the solvent is eliminated under reduced pressure at ambient temperature, the oily residue is taken up in isopropyl ether, left to crystallize at 4° C. separated and the product obtained is dried. 13.26 g of expected product is obtained. M.p.=84° C.

STAGE C

Ethyl 4-[2-(acetyloxy)-ethylthio]-2-butyl-1H-imidazole-5-carboxylate

The operation is carried out as indicated in stage D of Preparation 1 using 13.22 g of the product obtained in Stage B. 6.55 g of expected product is obtained. M.p.=68° C.

NMR Spectrum: $\underline{CH_3}-(CH_2)_2-CH_2$ 0.93 (t) $CH_3-(\underline{CH_2})_2-CH_2$ 1.39 (m) 1.71 (m) $CH_3-(CH_2)_2-\underline{CH_2}$ 2.71 (t) $CO_2-CH_2-\underline{CH_3}$ 1.39 (t) 4.35 (q) S—

CH₂—CH₂—O—CO— 3.41 (m) S—CH₂—CH₂—O—CO 4.35 (m) O—CO—CH₃ 2.08 (s) NH— 9.62

EXAMPLE 38

2-butyl-1-[[2'-carboxy-(1,1-biphenyl)-4-yl]methyl]-4-(2-hydroxy-ethylthio)-1H-imidazole-5-carboxylic acid The operation is carried out as in Example 2 starting with 254.4 mg of product obtained in Example 37. 147.4 mg of crude product is obtained which is recrystallized from 2 cm³ of isopropanol and 1 cm³ of water. In this way 120.7 mg of expected product is collected. M.p.=194° C.

NMR Spectrum: CH₃—(CH₂)₂—CH₂ 0.89 (t) CH₃—(CH₂)₂—CH₂ 1.36 (m) CH₃—CH₂—CH₂—CH₂ 1.68 (m) CH₃—(CH₂)₂—CH₂ 2.71 (t) C—S—(CH₂)₂—O 3.30 (m) 3.98 (m) CO₂Me 5.59 (s) N—CH₂—C₆H₄ 5.59 (s) Aromatics 7.03–7.84

EXAMPLE 39

Methyl 4'-[[2-butyl-4-(hydroxymethyl)-5-(phenylthio)-1H-imidazol-1-yl]-methyl]-(1,1'-biphenyl)-2-carboxylate The operation is carried out as in Example 1 starting with 474 mg of product obtained in the preparation indicated below and 610 mg of a bromine derivative, after chromatography on silica (eluant: methylene chloride - ethyl acetate (6-4 )), 530 mg of expected product, 4-hydroxymethyl-5-phenylthio isomer, and 225 mg of 5-hydroxymethyl-4-phenylthio isomer corresponding to the 4-hydroxymethyl-5-phenylthio isomer of Example 41, are obtained.

NMR Spectrum: DMSO 250 MHz CH₃—(CH₂)₂—CH₂ 0.88 (t) CH₃—(CH₂)₂—CH₂ 1.37 (m) 1.67 (m) CH₃—(CH₂)₂—CH₂ 2.65 (t) N—CH₂—C₆H₄ 5.15 (s) CH₂OH 4.77 (s) CO₂—CH₃ 3.62 (s) Aromatics 6.92 to 7.55 (m) 7.82 (dd)

Preparation of 2-butyl-4-phenylthio-1H-imidazole-5-methanol

The operation is carried out as in Preparation 3 using 609 mg of the imidazole prepared in stage B of Preparation 2 and 5 cm³ of a 1.2M solution of diisobutylaluminium hydride in toluene. 474 mg of expected product is obtained. M.p.=145° C.

EXAMPLE 40

4'-[[2-butyl-4-(hydroxymethyl)-5-(phenylthio)-1H-imidazol-1-yl]-methyl]-(1,1'-biphenyl)-2-carboxylic acid The operation is carried out as in Example 2 starting with 508 mg of product obtained as in Example 39 (5-phenylthio isomer), 386 mg of expected product is obtained. M.p.=220° C.

NMR Spectrum: DMSO 250 MHz CH₃—(CH₂)₃ 0.82 (t) CH₃—(CH₂)₂—CH₂ 1.28 (m)–1.56 (m) CH₃—(CH₂)₂—CH₂ 2.60 (m) N—CH₂—C₆H₄ 5.17 (s) CH₂—OH 4.44 (d, s after exchange) CO₂—H 12.75 (m) Aromatics 6.90 to 7.72

EXAMPLE 41

Methyl 4'-[[2-butyl-5-(hydroxymethyl)-4-(phenylthio)-1H-imidazol-1-yl]-methyl]-(1,1'-biphenyl)-2-carboxylate The product is obtained during the chromatography of Example 39.

225 mg of desired product is obtained.

NMR Spectrum: CDCl₃ 250 MHz CH₃—(CH₂)₃ 0.88 (t) CH₃—(CH₂)₂—CH₂ 1.35 (m)-1.70 (m) CH₃—(CH₂)₂—CH₂ 2.65 (m) N—CH₂—C₆H₄ 53.2 (s) CH₂—OH 4.60 (s) CO₂—CH₃ 3.62 (s) Aromatics 7.00 to 7.55; 7.84 (dd)

EXAMPLE 42

4'-[[2-butyl-5-(hydroxymethyl)-4-(phenylthio)-1H-imidazol-1-yl]-methyl]-(1,1'-biphenyl)-2-carboxylic acid The operation is carried out as in Example 2 starting with 183 mg of the product obtained in Example 41. 177 mg of product is obtained which is recrystallized from 1.77 cm³ of isopropanol and 0.17 cm³ of water. 103 mg of desired product is collected. M.p.=21 5° C.

| Analysis for $C_{24}H_{28}N_2O_3S$ = 424.57 | | | | |
|---|---|---|---|---|
| | C | H | N | S |
| % calculated | 71.16 | 5.97 | 5.92 | 6.78 |
| % found | 72.2 | 6.1 | 5.6 | 6.5 |

NMR Spectrum: DMSO 250 MHz CH₃—(CH₂)₃ 0.80 (t) CH₃—(CH₂)₂—CH₂ 1.26 (m)–1.52 (m) CH₃—(CH₂)₂—CH₂ 2.54 (masked) N—CH₂—C₆H₄ 5.38 (s) —CH₂—OH 4.49 (d, s after exchange) CO₂—H 12.75 (s,1) Aromatics 7.10 to 7.75 (m)

EXAMPLE 43

Ethyl 2-butyl-1-[[2'-carboxy-(1,1'-biphenyl)-4-yl]-methyl]-4-(2-fluoro-ethylthio)-1H-imidazole-5-carboxylate

STAGE A

Ethyl 2-butyl-1-[[2'-carboxy-(1,1'-biphenyl)-4-yl]-methyl]-4-[2-hydroxy-ethylthio]-1H-imidazole-5-carboxylate 10.17 g of product obtained in Example 37 is dissolved in 50 cm³ of ethanol, 47 cm³ of potassium carbonate (1M) is added slowly and agitation takes pace for 3 hours at ambient temperature. 1 liter of water is added, extraction takes place with ethyl acetate, the organic extracts are washed with salt water, dried and the solvent is eliminated under reduced pressure. After chromatographing on silica (eluant: ethyl acetate - methylene chloride (15-75)) 8.3 g of expected product is obtained.

NMR Spectrum: CDCl₃ 250 MHz CH₃—(CH₂)₃ 0.90 (t) CH₃—(CH₂)₂—CH₂ 1.34 (m) 1.70 (m) CH₃—(CH₂)₂—CH₂ 2.64 (m) CO₂—CH₂—CH₃ 1.34 (t) 4.30 (q) S—(CH₂)₂—O 3.29 (m) 4.02 (m) CO₂—CH₃ 3.62 (s) N—CH₂—C₆H₄ 5.57 (s) Aromatics 7.04 to 7.82

STAGE B

Ethyl 2-butyl-1-[[2'-carboxy-(1,1'-biphenyl)-
4-yl]methyl]-4-(2-fluoro-ethylthio)-1H-imidazole-
5-carboxylate 779.5 mg of diethyl amino sulphide trifluoride in 50 cm$^3$ of methylene chloride is cooled down to −78° C. 2 g of the product obtained in Stage A in 50 cm$^3$ of methylene chloride is added, the temperature is allowed to return to ambient, 1 liter of iced water is added and extraction takes place with ethyl acetate. The solvent is eliminated under reduced pressure, the residue is chromatographed on silica (eluant: acetone - methylene chloride (2 -98)). 1.06 g of expected product is obtained. M.p.=79° C.

NMR Spectrum: CDCl$_3$ CH$_3$—(CH$_2$)$_3$ 0.90 (t) CH$_3$—(CH$_2$)$_2$—CH$_2$ 1.33 (m) 1.67 (m) CH$_3$—(CH$_2$)$_2$—CH$_2$ 2.63 (m) CO$_2$—CH$_2$—CH$_3$ 1.33 (t) 4.27 (q) CO$_2$—CH$_3$ 3.62 (s) N—CH$_2$—C$_6$H$_4$ 5.55 (s) S—CH$_2$— 3.51 (dt, J=18 and 7) CH$_2$—F 4.70 (dt, J=47 and 7) Aromatics 7.03 to 7.82

EXAMPLE 44

2-butyl-1-[[2'-carboxy-(1,1'-biphenyl)-4-yl]-
methyl]-4-(2-fluoroethylthio)-1H-imidazole-
5-carboxylic acid 2.25 cm$^3$ of a 2N solution of sodium hydroxide is added at ambient temperature to 450 mg of the product obtained in Example 43 dissolved in 10 cm$^3$ of ethanol, then the mixture is left for 3 days. The solvents are evaporated under reduced pressure, the residue is taken up in water, 2.25 cm$^3$ of hydrochloric acid 2M/l is added. The precipitate formed is filtered, washed with water, dried under reduced pressure and 380 mg of expected product is obtained which is recrystallized from isopropanol. M.p.=185°–186° C.

| Analysis for C$_{24}$H$_{25}$FN$_2$O$_4$S = 456.54 | | | | |
|---|---|---|---|---|
| | C | H | F | N |
| % calculated | 63.14 | 5.52 | 4.16 | 6.13 |
| % found | 63.40 | 5.60 | 4.10 | 6.10 |

EXAMPLE 45

Ethyl
2-butyl-1-[[2'-carboxy-(1,1'-biphenyl)-4-yl]-methyl]-
4-(methylsulphinyl)-1H-imidazole-5-carboxylate The operation is carried out as in Example 15 starting with 1.55 g of the product obtained in Example 21 using 213 mg of metachloroperbenzoic acid. 1.8 g of crude product is obtained which is chromatographed on silica (eluant: methylene chloride - acetone (7-3)). 1.5 g of desired product is obtained.

| NMR Spectrum: CDCl$_3$ 250 MHz | |
|---|---|
| C<u>H</u>$_3$—(CH$_2$)$_2$—CH$_2$ | 0.90 (t) |
| CH$_3$—(C<u>H</u>$_2$)$_2$—CH$_2$ | 1.37 (m) 1.75 (m) |
| CH$_3$—(CH$_2$)$_2$—C<u>H</u>$_2$ | 2.74 (t) |
| S$_2$—CH$_3$ ‖ O | 2.97 (s) |
| —C<u>H</u>$_2$—C$_6$H$_4$ | 5.61 |

| NMR Spectrum: CDCl$_3$ 250 MHz | |
|---|---|
| CO$_2$—CH$_2$—CH$_3$ | 1.36 (t) 4.35 (q) |
| CO$_2$Me | 3.64 (s) |
| Aromatics | 7.04 to 7.84 |

EXAMPLE 46

2-butyl-1-[[2'-carboxy-(1,1'-biphenyl)-4-yl]methyl]-
4-(methylsulphinyl)-1H-imidazole-5-carboxylic acid The operation is carried out as in Example 2 starting with 380 mg of the product obtained in Example 45. 360 mg of product is obtained which is recrystallized from a mixture of 3 cm$^3$ of isopropanol and 1 cm$^3$ of water. 300 mg of desired product is obtained. M.p.=208° C.

| Analysis for C$_{23}$H$_{24}$N$_2$O$_5$S = 440.52 | | | | |
|---|---|---|---|---|
| | C | H | F | N |
| % calculated | 61.7 | 5.45 | 6.36 | 7.26 |
| % found | 63.0 | 5.5 | 6.3 | 7.20 |

| NMR Spectrum: DMSO 250 MHz | |
|---|---|
| C<u>H</u>$_3$—(CH$_2$)$_2$—CH$_2$ | 0.90 (t) |
| CH$_3$—C<u>H</u>$_2$—(CH$_2$)$_2$ | 1.36 (m) |
| CH$_3$—CH$_2$—C<u>H</u>$_2$—CH$_2$ | 1.70 (m) |
| CH$_3$—(CH$_2$)$_2$—C<u>H</u>$_2$ | 2.72 (m) |
| S—C<u>H</u>$_3$ ‖ O | 3.01 (s) |
| N—C<u>H</u>$_2$—C$_6$H$_4$ | 5.69 (s) |
| Aromatics | 7.05–7.85 |

EXAMPLE 47

Ethyl
2-butyl-1-[[2'-(methoxycarbonyl)-(1,1'-biphenyl)-
4-yl]-methyl]-4-(phenylmethylthio)-1H-imidazole-
5-carboxylate and the corresponding
5-(phenylmethylthio) isomer The operation is carried out as in Example 5, starting with 172 mg of the product obtained in the preparation below. 34 mg of product is obtained which is chromatographed on silica (eluant: methylene chloride - ethyl acetate (95-5)), 250 mg of desired product and 30 mg of the corresponding 5-phenylthio isomer are collected.

NMR Spectrum: CDCl$_3$ 300 MHz 1-4-(phenylmethylthio) isomer C<u>H</u>$_3$—(CH$_2$)$_2$—CH$_2$ 0.91 (t) CH$_3$—C<u>H</u>$_2$—(CH$_2$)$_2$ 1.36 (m) CH$_3$—CH$_2$—C<u>H</u>$_2$—CH$_2$ 1.71 (m) CH$_3$—(CH$_2$)$_2$—C<u>H</u>$_2$ 2.67 (m) CO$_2$Et 1.29 (t) 4.24 (q) CO$_2$Me 3.61 (s) S—C<u>H</u>$_2$—C$_6$H$_4$ 4.45 (d) N—C<u>H</u>$_2$—C$_6$H$_4$ 5.55 (s) Aromatics 7.01–7.82 2 -5-(phenylmethylthio) isomer C<u>H</u>$_3$—(CH$_2$)$_2$—CH$_2$ 0.87 (t) CH$_3$—C<u>H</u>$_2$—(CH$_2$)$_2$ 1.29 (m) CH$_3$—CH$_2$—C<u>H</u>$_2$—CH$_2$ 1.54 (m) CH$_3$—(CH$_2$)$_2$—C<u>H</u>$_2$ 2.55 (m) CO$_2$Et 1.47 (t) 4.48 (q) CO$_2$Me 3.60 (s) S—C<u>H</u>$_2$—C$_6$H$_4$ 4.02 (s) N—C<u>H</u>$_2$—C$_6$H$_4$ 4.74 (s) Aromatics 6.83–7.82

EXAMPLE 48

2-butyl-1-[[2'-carboxy-(1,1'-biphenyl)-4-yl]-methyl]-4-[(phenylmethyl)-thio]-1H-imidazole-5-carboxylic acid 214 mg of the product obtained in Example 47 is introduced into 4.28 ml of ethanol and 0.78 ml of soda (2N), the mixture is taken to reflux and agitated for 3 hours.

After drying under reduced pressure, the residue is dissolved in 5 ml of water, neutralization takes place by the addition of 0.78 ml of 2N hydrochloric acid, followed by agitation for approximately 15 minutes, separation and rinsing with water.

Recrystallization takes place from 1 ml of hot isopropanol with 0.5 ml of water added to it, after leaving for several hours at rest and separating. 170 mg of expected product is obtained. M.p.=190° C.

| | Microanalysis: | | | |
|---|---|---|---|---|
| | C | H | N | S |
| % calculated | 69.58 | 5.64 | 5.6 | 6.4 |
| % found | 69.5 | 5.7 | 5.7 | 6.4 |

IR Spectrum in NUJOL C=O 1662 cm$^{-1}$ Conjugated 1610 cm$^{-1}$ systems 1574 cm$^{-1}$ +aromatics 1500 cm$^{-1}$

EXAMPLE 49

Ethyl 2-butyl-4-(methylthio)-1-[[2'-cyano-(1,1'-biphenyl)-4-yl]-methyl]-1H-imidazole-5-carboxylate 0.5 g of ethyl 2-butyl-4-(methylthio)-1H-imidazole-5-carboxylate is introduced into 7.5 ml of dimethylformamide, 0.313 g of potassium bicarbonate and 0.616 g of 4'-(bromomethyl)-(1,1'-biphenyl)-2-carbonitrile and the mixture is left at ambient temperature for approximately 24 hours.

The whole is poured into 50 ml of water and 50 ml of ethyl acetate, followed by decanting, re-extracting with 2×50 ml of ethyl acetate, washing with 2×100 ml of water, drying, filtering and drying under reduced pressure.

After chromatography (eluant: methylene chloride - ethyl acetate (95-5)), and drying, 0.737 g of expected product is obtained.

IR Spectrum in chloroform —C≡O 2226 cm$^{-1}$ C=O 1690 cm$^{-1}$ aromatics 1600 -1597 -1560 -1509 -1500 cm$^{-1}$

EXAMPLE 50

Ethyl 2-butyl-4-(methylthio)-1-[[2'-(1H-tetrazol-5-yl)-(1,1'-biphenyl)-4-yl]-methyl]-1H-imidazole-5-carboxylate 1 g of the product obtained in Example 49 is introduced into 20 ml of xylene and approximately 1.3 to 1.7 g of trimethyltin nitride.

After approximately 40 to 48 hours at a temperature of approximately 115° C., the mixture is dried, taken up in 50 ml of water, extracted with 3×100 ml of methylene chloride, dried, filtered, and dried again.

After chromatography (eluant: methylene chloride - methanol (85-15)), and drying under reduced pressure, 858 mg of expected product is obtained.

IR Spectrum in chloroform =C—NH 3410 cm$^{-1}$ C=O 1688 cm$^{-1}$ Conjugated system 1615 -1600 -1575 cm$^{-1}$ +aromatic 1538 -1509 cm$^{-1}$

EXAMPLE 51

2-butyl-4-(methylthio)-1-[[2'-(1H-tetrazol-5-yl)-(1,1'-biphenyl)-4-yl]-methyl]-1H-imidazole-5-carboxylic acid 0.9 g of the product obtained in Example 50 is introduced into 9 ml of ethanol and 2.85 ml of soda (2N) is added.

The whole is left for approximately 1 hour under reflux, then dried, taken up in 7 ml of water and 2.85 ml of 2N hydrochloric acid is added.

The mixture is filtered, washed with water, dried, taken up in 23 ml of hot isopropanol, 25 ml of water is added whilst hot and the whole is left for approximately 48 hours at approximately 0° C., followed by filtering, washing with water and drying.

716 mg of expected product is obtained. M.p.=180° C.

| | Microanalysis: | | | |
|---|---|---|---|---|
| | C | H | N | S |
| % calculated | 61.58 | 5.39 | 18.73 | 7.14 |
| % found | 61.7 | 5.3 | 18.4 | 7.1 |

IR Spectrum in NUJOL Aromatics 1608 -1516 cm$^{-1}$ Heteroatom 1482 cm$^{-1}$

The products described in the table below which constitute Examples 52 to 113 correspond to the formula:

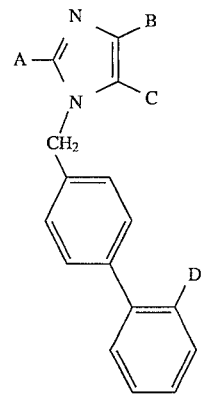

in which A, B and C have the meanings indicated in the table below and D represents the values, 1, 2, 3, 4, 5 and 6 such that 1 represents —CO$_2$Me, 2 represents —COOH, 3 represents —C≡N, 4 represents

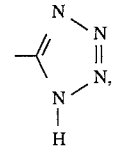

5 represents the salified tetrazole radical and 6 represents —CO$_2$tBu.

These products have been obtained according to the same processes as those indicated above. M.p.° C. designates the melting point of the products.

| N° Ex | A | B | C | D | Mp °C. |
|---|---|---|---|---|---|
| 52 | nBu | -S-C₆H₅ | -CH₂-O-C(CH₃)₂-O- | 1 | |
| | nBu | -CH₂-O-C(CH₃)₂-O- | -S-C₆H₅ | 1 | |
| 53 | nBu | -S(O)₂-C₆H₅ | -CH₂OH | 1 | 125 |
| 54 | nBu | " | " | 2 | 185 |
| 55 | nBu | " | -CH₂-O-C(CH₃)₂-O- | 1 | |
| 56 | nBu | " | " | 2 | ≈170 |
| 57 | nBu | -S-C₆H₅ | -CO₂Et | 1 | |
| 58 | nBu | " | " | 2 | |
| 59 | nBu | -S(O)₂-C₆H₅ | -CO₂Et | 1 | |
| 60 | nBu | " | -COOH | 1 | |
| 61 | nBu | -S(O)₂-(CH₂)₂-F | -CO₂Et | 1 | |
| 62 | nBu | -S(O)₂-(CH₂)₂-O-C₂H₅ | -COOH | 2 | 162 |
| 63 | nBu | -S-CH₃ | -CH₂OH | 1 | |
| | nBu | -CH₂-OH | -S-CH₃ | 1 | 132 |
| 64 | nBu | -S-CH₃ | -CH₂OH | 2 | 192 |
| 65 | nBu | -S(O)₂-CH₃ | -CH₂OH | 1 | |
| 66 | nBu | " | " | 2 | 210 |
| 67 | nBu | -S(O)₂-CH₂-CH₃ | -CO₂Et | 1 | |

-continued

| N° Ex | A | B | C | D | Mp °C. |
|---|---|---|---|---|---|
| 68 | nBu | " | —COOH | 2 | ≃195 |
| 69 | nBu | —CO$_2$Et | —S—CH$_2$—C$_6$H$_4$—OMe | 1 | |
|  | nBu | —S—CH$_2$—C$_6$H$_4$—OMe | —CO$_2$Et | 1 | |
| 70 | nBu | " | —COOH | 2 | 176 |
| 71 | nBu | —COOH | —S—CH$_2$—C$_6$H$_4$—OMe | 2 | 215 |
| 72 | nBu | —S—CH$_2$—C$_6$H$_5$ | —CH$_2$—O—C$_6$H$_4$—OMe | 1 | |
|  | nBu | —CH$_2$—O—C$_6$H$_4$—OMe | —S—CH$_2$—C$_6$H$_5$ | 1 | |
| 73 | nBu | —S—CH$_2$—C$_6$H$_5$ | —CH$_2$—OH | 1 | 122 |
|  | nBu | —CH$_2$—OH— | —S—CH$_2$—C$_6$H$_5$ | 1 | |
| 74 | nBu | —S—CH$_2$—C$_6$H$_5$ | —CH$_2$—OH | 2 | 120 |
| 75 | nBu | —CH$_2$—OH— | —S—CH$_2$—C$_6$H$_5$ | 2 | |
| 76 | nBu | —S—CH$_2$—C$_6$H$_5$ | —CHO | 1 | |
|  | nBu | —CHO | —S—CH$_2$—C$_6$H$_5$ | 1 | |
| 77 | nBu | —S(O)$_2$—CH$_2$—C$_6$H$_5$ | —CH$_2$—OH | 1 | 172 |
| 78 | nBu | " | " | 2 | 200 |
| 79 | nBu | —S(O)$_2$—(CH$_2$)$_2$—OH | —CO$_2$Et | 1 | 79 |
| 80 | nBu | " | —COOH | 2 | 130 |

-continued
| N° Ex | A | B | | C | | D | Mp °C. |
|---|---|---|---|---|---|---|---|
| 81 | nBu | 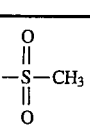 | | —CO$_2$Et | | 3 | |
| 82 | nBu | " | | " | | 4 | |
| 83 | nBu | " | | —COOH | | 4 | 160 |
| 84 | nBu | " | | —COO—K | | 5 | ≃250 |
| 85 | nBu | 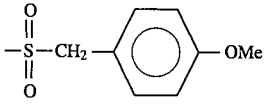 | | —CO$_2$Et | | 1 | ≃210 |
| 86 | nBu | " | | —COOH | | 2 | 200 |
| 87 | nBu | 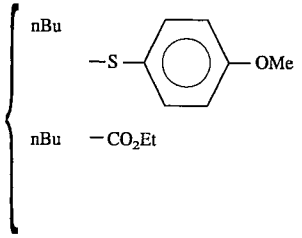 | | —CO$_2$Et | | 1 | |
|  | nBu | —CO$_2$Et | | 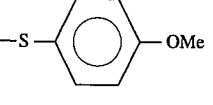 | | 1 | |
| 88 | nBu | 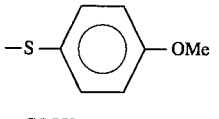 | | —COOH | | 2 | 174 |
| 89 | nBu | —COOH | | 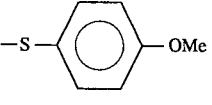 | | 2 | |
| 90 | nBu | 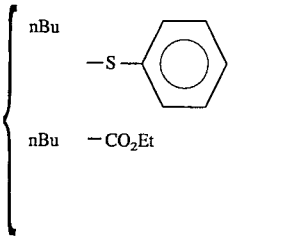 | | —CO$_2$Et | | 3 | |
|  | nBu | —CO$_2$Et | | 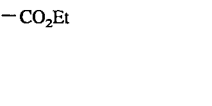 | | 3 | |
| 91 | nBu | 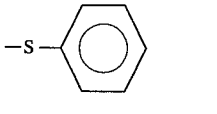 | | —CO$_2$Et | | 4 | |
| 92 | nBu | " | | —COOH | | 4 | 144 |
| 93 | nBu | 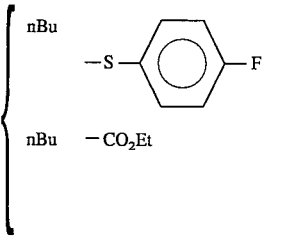 | | —CO$_2$Et | | 1 | |
|  | nBu | —CO$_2$Et | | 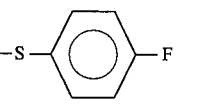 | | 1 | |
| 94 | nBu | 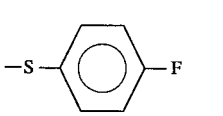 | | —COOH | | 2 | 214 |
| 95 | nBu | —S—nBu | | —CO$_2$Et | | 1 | |
| 96 | nBu | " | | —COOH | | 2 | 178 |

| N° Ex | A | B | C | D | Mp °C. |
|---|---|---|---|---|---|
| 97 | nBu | —S—C₆H₅ | H | 1 | |
| | nBu | —H | —S—C₆H₅ | 1 | |
| 98 | nBu | —S—C₆H₅ | H | 2 | 218 |
| 99 | nBu | —S—CH₂—C₆H₄—OMe | —CHO | 1 | |
| | nBu | —CHO | —S—CH₂—C₆H₄—OMe | 1 | |
| 100 | nBu | —S—CH₂—C₆H₄—OMe | —CH₂OH | 1 | 120 |
| 101 | nBu | " | " | 2 | 125 |
| 102 | nBu | —S(O)₂—CH₂—C₆H₄—OMe | " | 1 | |
| 103 | nBu | " | " | 2 | 192 |
| 103 | nBu | —S—CH₃ | —COOH | 3 | |
| 105 | nBu | " | —C(O)—O—CH₂—O—C(O)-tBu | 3 | |
| 106 | nBu | " | " | 4 | 142 |
| 107 | nBu | —S—CH₂—C₆H₄—CF₃ | —CO₂Et | 1 | |
| | nBu | —CO₂Et | —S—CH₂—C₆H₄—CF₃ | 1 | |
| 108 | nBu | —S—CH₂—C₆H₄—CF₃ | —COOH | 2 | 188 |
| 109 | nBu | —S(O)—CH₃ | —CO₂tBu | 6 | |
| 110 | nBu | —S—CH₂—F | " | 6 | |
| 111 | nBu | " | —COOH | 2 | 192 |
| 112 | nBu | —S—CF₃ | —CO₂Et | 1 | |
| 113 | nBu | " | —COOH | 2 | 200 |

Moreover the following products which constitute Examples 114 to 143 may be obtained by the process indicated above

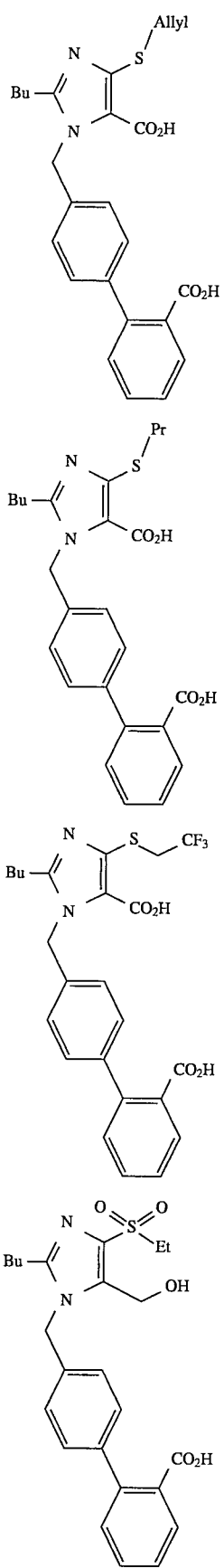
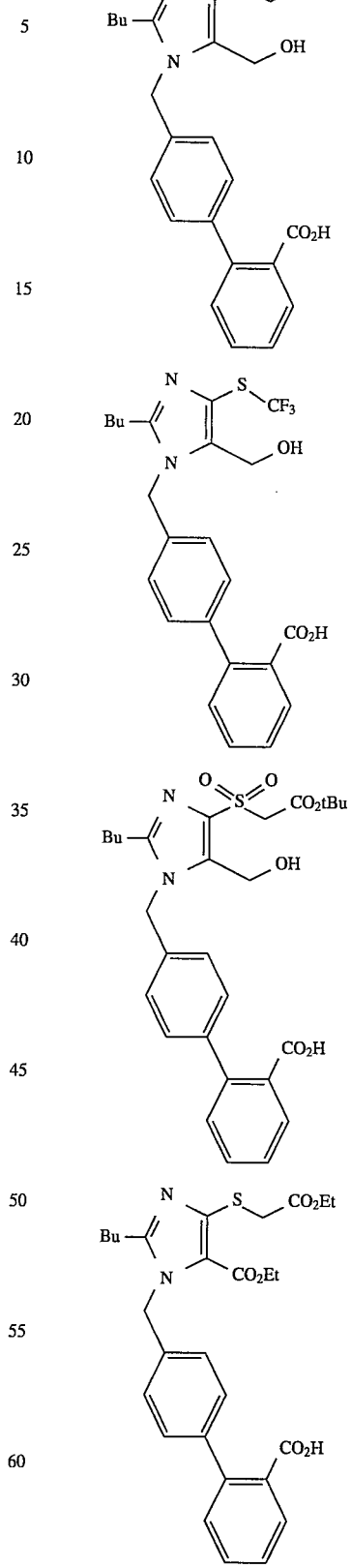

65
-continued
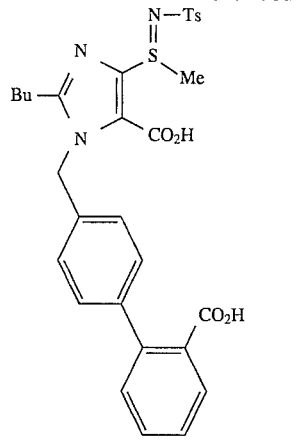
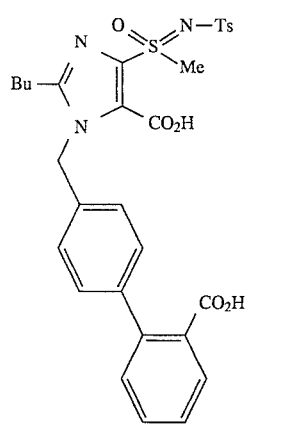
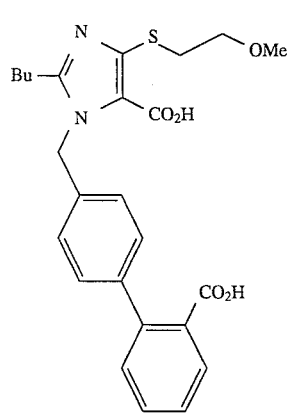
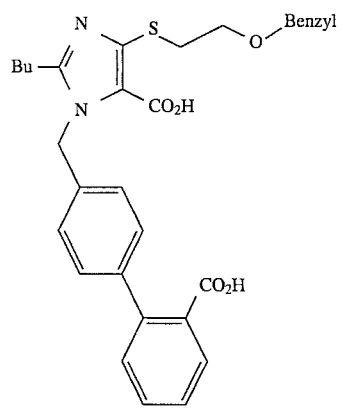
66
-continued
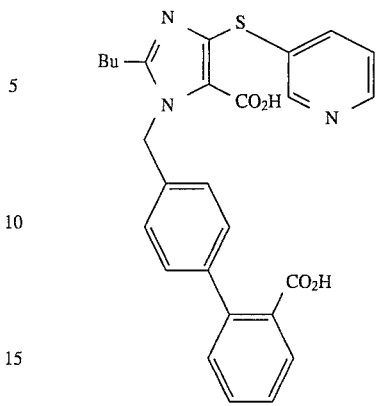
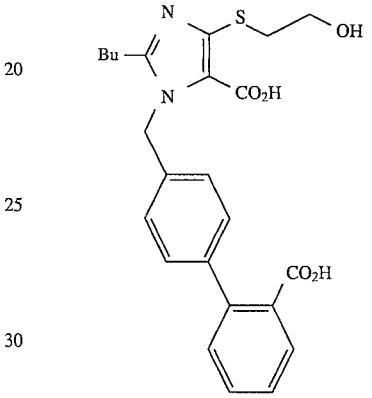
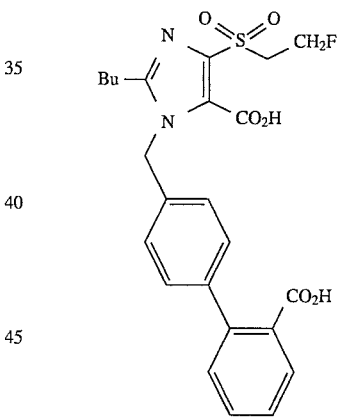
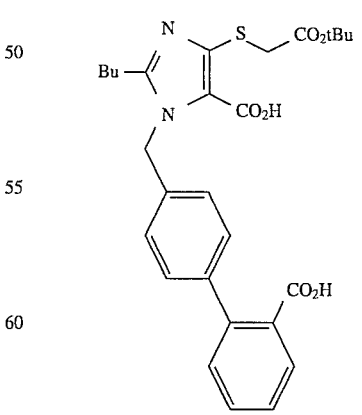

67
-continued
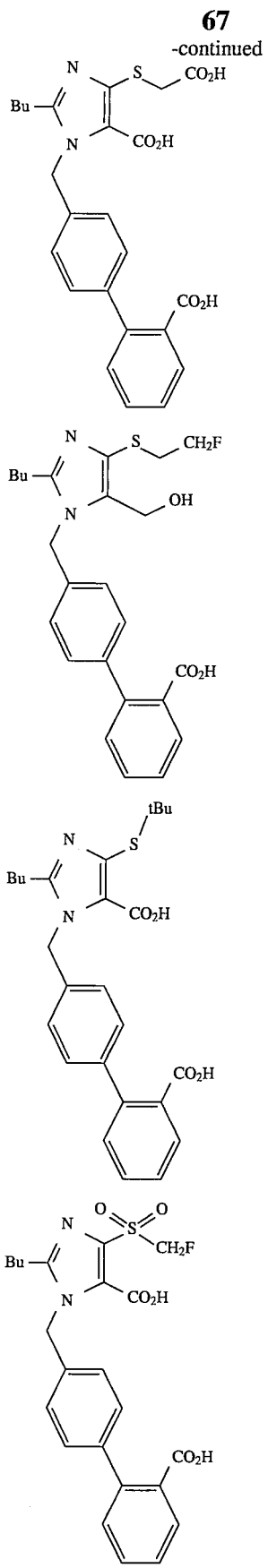
68
-continued
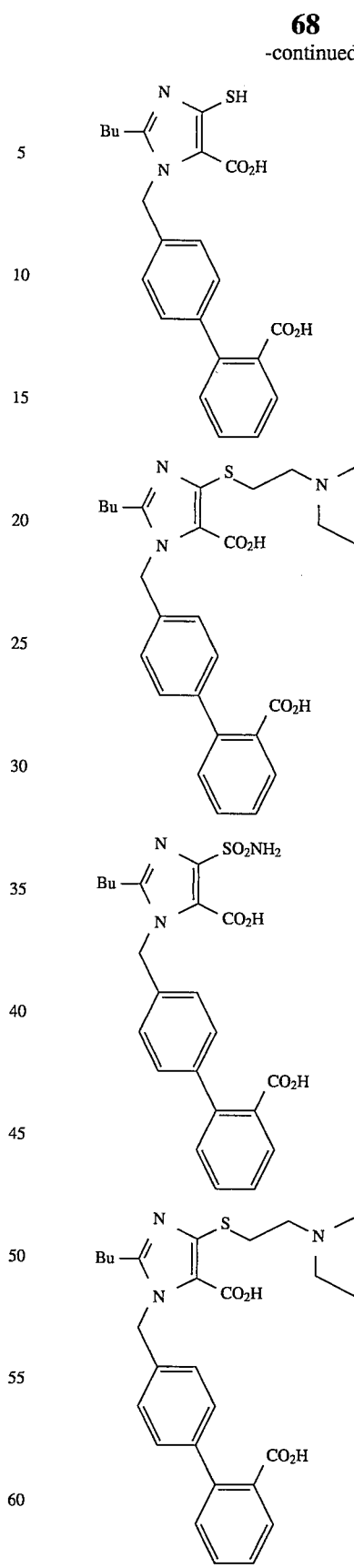

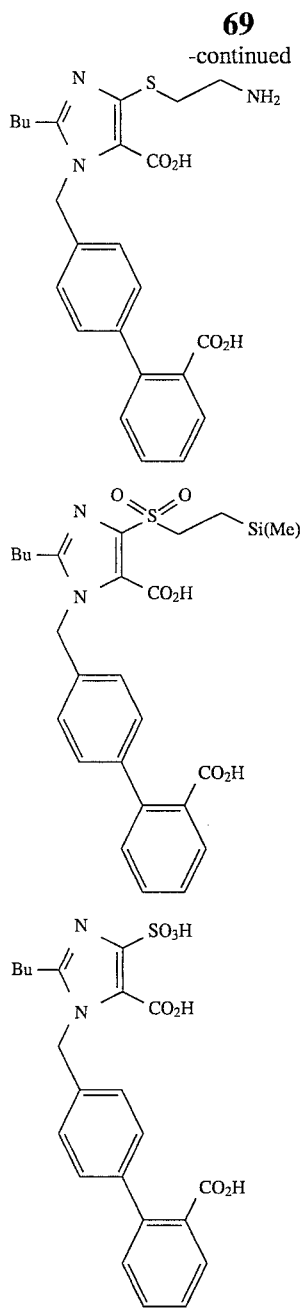

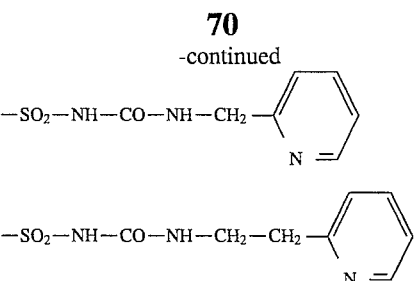

The following 4 producLs have notably been prepared following the experimental conditions described above and constituted the following Examples 144 to 147

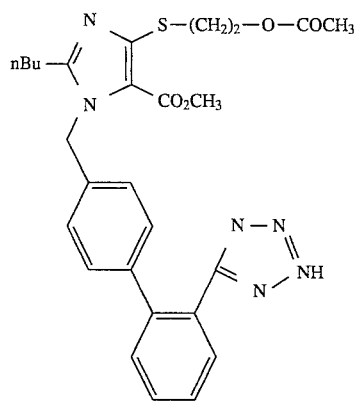

144

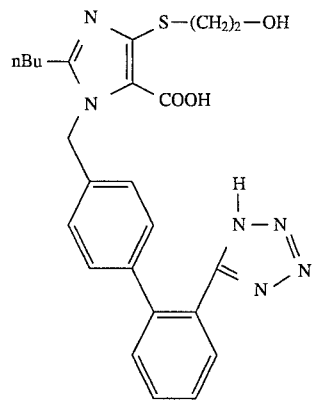

145

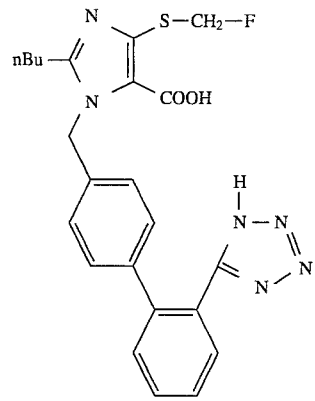

146

The products described in the Examples above can also, and notably in the place of the carboxy substituent that is carried by the biphenyl radical linked by a methylene radical to a nitrogen atom of the imidazole radical, contain an optionally salified tetrazole radical or a —$(CH_2)_{m1}$—$S(O)_{m2}$—X—$R_{10}$ radical, as defined above and quite particularly the radicals:

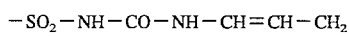

147

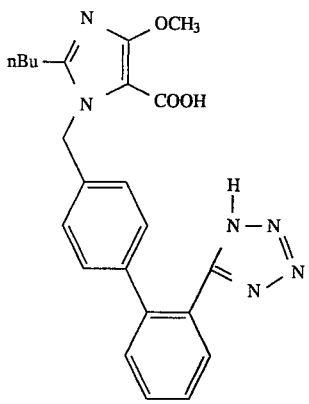

The product of Example 145 as defined above can be characterized by the following analytical results:

| IR cm$^{-1}$ Nujol: | |
|---|---|
| OH/NH | : 1660 cm$^{-1}$ |
| absorption =O | |
| conjugated | 1604 cm$^{-1}$ |
| system + | 1574 cm$^{-1}$ |
| aromatics | 1520 cm$^{-1}$ |

UV in EtOH for MM=478.56 infl. 225 nm epsilon=28900 infl. 246 nm epsilon=16500 max. 282 nm epsilon=14700

Among the products of formula (I) as defined above which constitute products able to be obtained within the scope of the present invention, the preferred products are those in which $R_2$ represents an -Alk radical and $R_3$ represents an —S(O)Alk radical, as well as those in which $R_2$ represents a sulphurous radical, notably

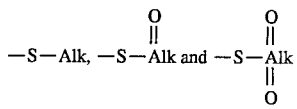

or an O-Alk radical and $R_3$ represents a —COOH or —CH$_2$OH radical, the —Alk radical in the above radicals representing a linear or branched alkyl radical containing at most 4 carbon atoms and optionally substituted by one or more radicals chosen from halogen atoms; the hydroxyl radical; the amino radical itself optionally substituted by one or two alkyl radicals containing at most 4 carbon atoms; the phenyl radical itself optionally substituted by one or more radicals chosen from alkyl or alkoxy radicals containing at most 4 carbon atoms, halogen atoms, cyano, nitro, free, salified or esterified carboxy and tetrazolyl radicals.

EXAMPLE 144 of pharmaceutical composition

Tablets were prepared corresponding to the following formula:

| Product of Example 51 | 50 mg |
|---|---|
| Excipient for a tablet completed at | 200 mg |
| (detail of excipient: lactose, talc, starch, magnesium stearate). | |

PHARMACOLOGICAL RESULTS

1—Test on the angiotensin II receptor

A fresh membrane preparation obtained from the liver of a rat is used. The tissue is ground up in a polytron in a Tris 50 mM buffer pH 7.4, the grinding is followed by 3 centrifugations at 30,000 g for 15 minutes, the deposits being taken up in between in the Tris buffer pH 7.4.

The last deposits are put in suspension in an incubation buffer (Tris 20 mM, NaCl 135 mM, KCl 10 mM, glucose 5 mM, MgCl$_2$ 135 mM, KCl 10 mM, glucose 5 mM, MgCl$_2$ 10 mM PMSF 0.3 mM, bacitracin 0.1 mM, BSA 0.2%).

Aliquoted fractions of 2 ml are divided into hemolysis tubes and I$^{125}$ angiotensin II (25,000 DPM per tube) and the product to be studied are added. (The product is first tested at 3×10$^{-5}$M three times). When the tested product displaces by more than 50% the radioactivity linked specifically to the receptor, it is tested again according to a range of 7 doses in order to determine the dose which inhibits by 50% the radioactivity linked specifically to the receptor. In this way the 50% inhibiting concentration is determined.

The non-specific bond is determined by addition of the product of Example 94 of the European Patent 0,253,310, at 10$^{-5}$M (three times). The medium is incubated at 25° C. for 150 minutes, put in a water bath at 0° C. for 5 minutes, filtered under vacuum, rinsed with Tris buffer pH 7.4 and the radioactivity is counted in the presence of scintillating Triton.

The result is expressed directly as the 50% inhibiting concentration (IC$_{50}$), that is as the concentration of studied product, expressed in nM, necessary to displace 50% of the specific radioactivity fixed on the receptor studied.

| Results: | |
|---|---|
| Product of Example | IC$_{50}$ in nanomoles |
| 28 | 10.2 |
| 20 | 17.0 |
| 26 | 47.0 |
| 22 | 49.0 |
| 48 | 5.7 |
| 70 | 3.6 |
| 74 | 5.8 |
| 51 | 1.9 |
| 83 | 1.3 |
| 92 | 0.5 |
| 84 | 0.8 |

2—Revealing the antagonistic activity of angiotensin II on the isolated portal vein The portal vein of male Wistar rats (about 350 g) (IFFA Credo France) is removed after cervical dislocation and placed rapidly in a physiological solution (see below) at ambient temperature. A ring of about 1 mm is mounted in a bath with an isolation mechanism, containing 20 ml of the following physiological solution (composition in mM: NaCl 118.3 - KCl 4.7 - MgSO$_4$ 1.2 - KH$_2$PO$_4$ 1.2 - NaHCO$_3$ 25 - glucose 11.1 - CaCl$_2$ 2.5), the medium is maintained at 37° C. and oxygenated with an oxygen (95%), carbon dioxide (5%) mixture. The initial pressure imposed is 1 g, the rings are left at rest for 60 to 90 minutes. In order to avoid spontaneous contractions, verapamil is added to the incubation bath (1.10$^{-6}$M).

At the end of the rest period angiotensin II (Ciba hypertensin) 3.10⁻⁸M is added to the incubation bath and left in contact with the preparation for one minute. This operation is repeated every 30 minutes, the tissue being washed 3 or 4 times between two stimulations by angiotensin. The compound to be studied is introduced into the bath 15 minutes before a new stimulation by angiotensin. Increasing concentrations of the product to be studied are used and the $IC_{50}$ (dose which produces a 50% inhibition of the response to angiotensin) of the product to be studied is calculated, this is expressed in nanomoles.

| Results: | |
|---|---|
| Product of Example | $IC_{50}$ in nanomoles |
| 20 | 5 |
| 22 | 8 |
| 14 | 10 |
| 6 | 13 |
| 48 | 0.9 |
| 70 | 0.56 |
| 74 | 2 |
| 51 | 0.14 |
| 83 | 0.21 |

3—Test for antagonistic activity of angiotensin II in a demedullated rat

Male Sprague-Dawley rats (250 to 350 g) are anaesthetized by an intra-peritoneal injection of sodium pentobarbital (60 mg/kg). The diastolic arterial pressure is recorded by means of a heparinized catheter (PE50) introduced into the left carotid of the animal, and connected to a pressure calculator (Gould, Pressure Processor) by means of a Gould pressure sensor.

A catheter is introduced into the right jugular vein of the animal in order to allow the injection of the molecules to be studied.

The animal is placed under assisted respiration. A bilateral section of the pneumogastric nerves is carried out. The rat is then demedullated.

After a suitable period of stabilization, the study of the antagonism of the molecules vis- -vis angiotensin II (CIBA Hypertensin) is approached in the following manner:

1—Three consecutive injections of angiotensin II (0.75 micrograms/kg) spaced 15 minutes apart permits a reproducible and stable pressure response to be obtained.

2—While keeping a time interval of 15 minutes for the administration of angiotensin II, the molecules (0.01 to 10 mg/kg) are injected 5 minutes before the angiotensin II.

The pressure effects of angiotensin II in the presence of the antagonist are expressed as a percentage of the pressure effects of angiotensin II administered on its own. The dose which inhibits the studied effect by 50% is thus determined.

Each animal is considered to be its own control.

| Results: | |
|---|---|
| Product of example | $IC_{50}$ in mg/kg |
| 16 | 0.29 |
| 22 | 0.47 |
| 14 | 0.78 |
| 18 | 0.79 |
| 70 | 0.33 |
| 74 | 0.34 |
| 51 | 0.054 |
| 83 | 0.022 |
| 92 | 0.08 |
| 106 | 0.04 |

We claim:

1. A compound selected from the group consisting of a compound of the formula

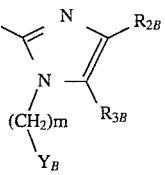

wherein $R_1$ is alkyl of 1 to 13 carbon atoms, $R_{2B}$ is selected from the group consisting of S-alkyl of 1 to 4 carbon atoms, S-alkenyl of 2 to 4 carbon atoms, hydrogen, acyl of an organic carboxylic acid of 1 to 6 carbon atoms, alkoxy and alkoxyalkyl of up to 6 carbon atoms and carboxy, $R_{3B}$ is selected from the group consisting of hydrogen, acyl of an organic carboxylic acid of up 6 carbon atoms, $—S(O)_n—$Alk and $—S(O)_n$-phenyl, n is 0, 1 or 2, Alk is alkyl of 1 to 4 carbon atoms, m is 1, $Y_B$ is

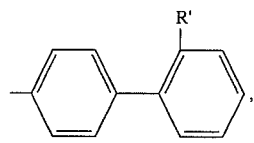

R' is selected from the group consisting of —COOH or tetrazolyl and their non-toxic, pharmaceutically acceptable salts with acids and bases.

2. A compound of claim 1 wherein $R_3$ is $—S(O)_n—$Alk or $—S(O)_n$-phenyl.

3. A compound of claim 1 selected from the group consisting of 2-butyl-1-[[2'-carboxy-(1,1'-biphenyl)-4-yl]-methyl]-4-(phenylthio)-1H-imidazole-5-carboxylic acid and 4'-[[2-butyl-4-(ethylthio)-5-(hydroxymethyl)-1H-imidazol-1-yl]-methyl]-(1,1'-biphenyl)-2-carboxylic acid and their non-toxic, pharmaceutically acceptable acid addition salts.

4. A method of inhibiting angiotension II effects in warm-blooded animals comprising administering to warm-blooded animals an amount of a compound of claim 1 sufficient to inhibit angiotension II effects.

* * * * *